US010589059B2

(12) United States Patent
Frey et al.

(10) Patent No.: US 10,589,059 B2
(45) Date of Patent: Mar. 17, 2020

(54) INSERTION DEVICE WITH PROTECTION AGAINST REUSE

(71) Applicant: Roche Diabetes Care, Inc., Indianapolis, IN (US)

(72) Inventors: Stephan-Michael Frey, Pfungstadt (DE); Oliver Kube, Worms (DE); Andrea Rittinghaus, Neckarsteinach (DE)

(73) Assignee: ROCHE DIABETES CARE, INC., Indianapolis, IN (US)

(*) Notice: Subject to any disclaimer, the term of this patent is extended or adjusted under 35 U.S.C. 154(b) by 420 days.

(21) Appl. No.: 15/327,052

(22) PCT Filed: Jul. 22, 2015

(86) PCT No.: PCT/EP2015/066722
§ 371 (c)(1),
(2) Date: Jan. 18, 2017

(87) PCT Pub. No.: WO2016/012482
PCT Pub. Date: Jan. 28, 2016

(65) Prior Publication Data
US 2017/0165451 A1 Jun. 15, 2017

(30) Foreign Application Priority Data

Jul. 22, 2014 (EP) .................................. 14177972

(51) Int. Cl.
*A61M 5/158* (2006.01)
*A61M 25/00* (2006.01)
*A61M 5/50* (2006.01)

(52) U.S. Cl.
CPC ............ *A61M 25/00* (2013.01); *A61M 5/158* (2013.01); *A61M 5/50* (2013.01);
(Continued)

(58) Field of Classification Search
CPC .................... A61M 5/158; A61M 5/50; A61M 2005/1583–1585; A61M 2205/273; A61B 2560/063; A61B 5/14503; A61B 17/3468
See application file for complete search history.

(56) References Cited

U.S. PATENT DOCUMENTS 7,611,497 B2    11/2009  Wollschlager
9,629,958 B2     4/2017  Deck et al.
(Continued)

FOREIGN PATENT DOCUMENTS

EP    2 174 680 A1    4/2010
EP    2 429 382 B1    5/2010
(Continued)

*Primary Examiner* — Devin B Henson
*Assistant Examiner* — H. Q. Nguyen
(74) *Attorney, Agent, or Firm* — Woodard, Emhardt, Henry, Reeves & Wagner LLP

(57) ABSTRACT

An insertion device (110) for inserting an analyte sensor (114) into a body tissue is proposed. The insertion device (110) comprises an insertion needle holder (120) and a drive mechanism (124) for linearly driving the insertion needle holder (120) in a longitudinal direction (126). The drive mechanism (124) comprises at least one actuator (132) for actuating the drive mechanism (124). The actuator (132) comprises at least one actuator arm (136, 138) which is pivotable about at least one axle (140) in order to actuate the drive mechanism (124). The insertion device (110) further comprises at least one protection against reuse including at least one locking mechanism (178). The locking mechanism (178) is adapted to at least partially prevent a back-pivoting of the actuator arm (136, 138) in a direction reversing the actuation direction once the actuator arm (136, 138) has been pivoted by at least one threshold angle.

12 Claims, 14 Drawing Sheets

(52) U.S. Cl.
CPC ............ *A61M 2005/1583* (2013.01); *A61M 2005/1585* (2013.01); *A61M 2205/273* (2013.01)

(56) References Cited

U.S. PATENT DOCUMENTS

| | | |
|---|---|---|
| 9,662,071 B2 * | 5/2017 | Ohkoshi .............. A61B 5/0031 |
| 9,750,898 B2 * | 9/2017 | Davies ................... A61M 5/24 |
| 2010/0137695 A1 * | 6/2010 | Yodfat ................. A61B 5/6849 |
| | | 600/345 |
| 2010/0230285 A1 | 9/2010 | Hoss et al. |
| 2011/0021889 A1 | 1/2011 | Hoss et al. |

FOREIGN PATENT DOCUMENTS

| | | |
|---|---|---|
| WO | WO 2005/078424 A1 | 8/2005 |
| WO | WO 2007/071562 A1 | 6/2007 |
| WO | WO 2009/033032 A1 | 3/2009 |
| WO | WO 2010 072290 A1 | 7/2010 |
| WO | WO 2014/001382 A1 | 1/2014 |

\* cited by examiner

INSERTION DEVICE WITH PROTECTION AGAINST REUSE

FIELD OF THE INVENTION

The invention relates to an insertion device for inserting an analyte sensor and to a method for inserting an analyte sensor. Devices and methods according to the present invention are mainly used in the field of glucose monitoring, both for home monitoring purposes and for monitoring in hospitals or other healthcare institutions or nursing homes. It shall be noted, however, that other applications are feasible, such as applications in monitoring one or more other types of analytes besides or in addition to glucose.

RELATED ART

In the field of diagnostics and therapeutics, besides so-called spot monitoring devices requiring a single sample of a body fluid such as blood or interstitial fluid, a large number of devices for long-term monitoring or continuous monitoring are known. In these devices, generally, analyte sensors are fully or partially implanted into a body tissue of a user. Thus, mainly, transcutaneous analyte sensors are used which extend, from a portion outside the body of a user, through the skin of the user into a body tissue. These sensors, mainly by using electrochemical measurements, are capable of generating a sensor signal indicating a concentration of one or more analytes in the body tissue or in a body fluid contained within the body tissue. Examples of these type of implantable sensors which may also be used within the present invention are disclosed e.g. in WO 2007/071562 A1, US 2011/0021889 A1, US 2010/0230285 A1, in WO 2005/078424 A1 or in WO 2014/001382 A1. Other types of analyte sensors, however, may be used.

In the field of transcutaneous sensors, the implantation or insertion of the analyte sensors into the body tissue of the user remains a technical challenge. Meanwhile, several insertion devices are known in the art or are even commercially available. Thus, insertion devices are commercially available by Dexcom, Inc., San Diego, USA, such as a part of the Dexcom G4 Platinum System. Other insertion devices are commercially available by Abbott GmbH & Co. KG, Wiesbaden, Germany, such as under the trade name Abbott Navigator.

Further, EP 2 429 382 B1 discloses an insertion device for subcutaneous insertion of a device into a body tissue. The insertion device has at least one insertion aid and at least one subcutaneous device, wherein the insertion aid has at least one substantially rigidly designed base body, such as an insertion needle, for insertion into the body tissue. The insertion device is designed to generate an adjustable holding force between the base body and the subcutaneous device and is further designed to set the holding force during the insertion such that the subcutaneous device is held against the base body. The insertion device is furthermore designed to set the holding force after the insertion such that the subcutaneous device is detachable from the base body.

In EP 2 174 680 A1, an insertion device is disclosed, having an insertion needle holder and a drive mechanism for driving the insertion needle holder into a puncture direction in a linear fashion. The insertion device further comprises at least one actuation element for actuating the drive mechanism. The drive mechanism is adapted to transform an actuation motion of the actuation element in a transverse direction into a puncture motion of the insertion needle holder.

In WO 2010/072290 A1, an insertion system is disclosed, having a base unit for placing on the body of a patient and an insertion device which may be coupled to the base unit. The insertion device comprises an insertion needle holder for holding an insertion needle and a drive mechanism for displacing the insertion needle holder in a pricking direction. The device further comprises a locking mechanism causing locking of the drive mechanism in an active state and being set to an inactive state in which the locking is released by coupling the insertion device to the base unit.

US 2009/099521 A1 discloses a cannula insertion device including a housing defining an opening for receiving therethrough a cannula and further defining a channel, and a cannula forming a lumen. The cannula is adapted for sliding movement within the housing from a retracted position to an extended position. When the cannula is in the retracted position, the lumen is located remotely from the channel and the channel is in fluidic communication with the opening. When the cannula is in the extended position, the lumen is in fluidic communication with the channel.

Despite the progress that has been made in the field of insertion devices, several technical challenges remain. Thus, the systems and devices still have to provide a technically simple setup for insertion with as little parts as possible. Several of the commercially available insertion devices, however, lead to the unwanted situation in which several lose parts remain after insertion. The insertion devices known today, additionally, generally require a plurality of separate handling steps which, specifically for children and elderly persons or handicapped persons, provide some severe difficulties.

In other cases, the insertion device is provided in a pre-tensioned fashion, such as with a pre-tensioned spring element. This setup, however, has to face the technical challenge that the pre-tensioning has to be sufficient to penetrate any kind of skin. Therefore, the pre-tensioning of the spring elements has to be oversized, in order to provide penetration for even the toughest type of skin. This over-dimensioning, however, implies the disadvantage that a needle holder, during insertion, impetuously abuts on a stopper of the insertion device which may lead to an increase of the subjective feeling of pain during insertion.

Further, many known devices generally are prone to misuse and faulty operation. This technical challenge specifically has to be considered in the context of diabetes care, since many patients suffering from diabetes suffer from diabetes-related handicaps. Many known devices, however, allow for a faulty operation in which the insertion device is placed onto the skin of the user and partially operated, followed by an interruption of the insertion process. Thereby, partially fired insertion devices may occur, having contaminated insertion needles, which imply the risk of unwanted and dangerous reuse of the contaminated insertion needle or the risk of injuries incurred by the contaminated needle.

Consequently, there remains a need for insertion devices, insertion kits and insertion methods which address the above-mentioned technical challenges. Specifically, a need for an insertion device remains which is easy to handle even by elderly people, children or handicapped people, which is adapted to cope with any type of skin, which provides a smooth and painless operation and which provides a protection against reuse, misuse and injuries.

Problem to be Solved

It is therefore an objective of the present invention to provide an insertion device, an insertion kit and a method for inserting an analyte sensor into a body tissue which address the above-mentioned challenges and which solve the above-mentioned problems of known devices and methods. Specifically, an insertion device, an insertion kit and a method shall be provided which are easy to handle even by elderly people, children or handicapped people, which are adapted to cope with any type of skin, which provide a smooth and painless operation and which provide a protection against reuse, misuse and injuries.

SUMMARY OF THE INVENTION

This problem is solved by an insertion device, an insertion kit and a method with the features of the independent claims. Preferred embodiments, which might be realized in an isolated fashion or in any arbitrary combination are listed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present invention, an insertion device for inserting an analyte sensor into a body tissue is disclosed. As used herein, an insertion device generally refers to a device which is capable of fully or partially implanting or inserting an analyte sensor into the body tissue. As will be outlined in further detail below, the insertion device specifically may be adapted to transcutaneously or subcutaneously insert an analyte sensor into a body tissue, such as by performing an incision or a puncture in a skin of the user or patient and by transferring the analyte sensor fully or partially into the body tissue. The insertion device specifically may be a transcutaneous insertion device. As will be outlined in further detail below, the insertion device specifically may be a mechanical insertion device which preferably may be operated by hand, preferably without the need of electrical or electromechanical actuators. However, other embodiments are feasible.

As further used herein, an analyte sensor generally refers to a sensor which is capable of qualitatively or quantitatively detecting the presence and/or the concentration of at least one analyte in the body tissue and/or in a body fluid contained within the body tissue. Specifically, the analyte sensor may be an electrochemical analyte sensor, having at least two electrodes, such as at least one working electrode and at least one further electrode such as at least one counter electrode and/or at least one reference electrode. The working electrode may comprise a working electrode pad and, optionally, at least one test chemical disposed thereon. The at least one further electrode, such as the at least one counter electrode and/or the at least one reference electrode, may comprise a conductive electrode pad, too. Additionally and optionally, one or more redox materials may be disposed thereon. For potential embodiments of analyte sensors, reference may be made to the above-mentioned prior art documents. Specifically, the electrochemical sensor strips which are implantable into a body tissue, as disclosed in one or more of these prior art documents, may also be used within the present invention. Specifically, the analyte sensor may be a strip-shaped analyte sensor having a flexible substrate and the at least two electrodes disposed thereon. As an example, the analyte sensor may have a length of 5 mm to 50 mm, specifically a length of 7 mm to 30 mm. The analyte sensor may further provide a biocompatible cover, such as a biocompatible membrane which fully or partially covers the analyte sensor and which prevents the test chemical from migrating into the body tissue and which allows for a diffusion of the body fluid and/or the analyte to the electrodes. For potential embodiments of the membrane, reference may be made to the above-mentioned prior art documents. Other embodiments are feasible. The analyte sensor may further provide one or more leads for electrically contacting the electrodes. The leads may, during insertion or at a later point in time, be connected to one or more measurement devices adapted for measuring electrical currents and/or electrical voltages, such as to one or more potentiostats.

The analyte, as outlined above, specifically may be an analyte which takes part in the metabolism of a body of a user. Specifically, the analyte may be a metabolite or a combination of two or more metabolites. As an example, the analyte may be selected from the group consisting of: glucose, lactate, triglycerides, cholesterol. Still, other analytes or combinations of two or more analytes may be detected.

The body tissue specifically may be or may comprise fatty tissue. Other types of body tissue, however, are feasible.

The insertion device comprises an insertion needle holder. As used herein, an insertion needle holder generally is a component or a combination of components of the insertion device which is capable of holding a needle for insertion. Specifically, the needle may be or may comprise a cannula, and the needle may be a further optional part of the insertion device or may form an independent part. The needle holder may be or may comprise at least one plunger or push rod or may be connected to at least one plunger or push rod in order to drive the insertion needle to perform a puncture or insertion motion into the body tissue and back.

The insertion device further comprises at least one drive mechanism for linearly driving the insertion needle holder in a longitudinal direction. As used herein, a drive mechanism generally refers to a device or combination of devices adapted for actuating the insertion needle holder such that the insertion needle holder performs a motion. The drive mechanism specifically may be adapted for driving the insertion needle holder to perform a linear motion. As defined herein, a longitudinal direction is defined by the insertion of the analyte sensor into the body tissue. Thus, specifically, the longitudinal direction may be a direction of puncture during a puncture motion of the insertion needle during inserting the analyte sensor into the body tissue, or a reverse direction. Thus, during insertion, the insertion needle may perform a puncture motion in the longitudinal direction, thereby creating an incision in a skin of a user or patient, transferring the analyte sensor into the body tissue, and, subsequently, a motion into the reverse direction, wherein the insertion needle is pulled out from the body tissue, wherein the analyte sensor remains within the body tissue. During insertion, the analyte sensor may fully or partially be surrounded by the insertion needle. The drive mechanism, as outlined above, may be or may comprise at least one plunger or push rod which is adapted for pushing the insertion needle to perform the puncture motion and which may further be adapted to pull back the insertion needle after insertion.

The drive mechanism comprises at least one actuator for actuating the drive mechanism. As used herein, an actuator generally refers to a transformer which is adapted to transform an energy or force into a motion of the drive mechanism, specifically a motion of the plunger and/or push rod of the drive mechanism. The energy may be stored in an energy storage and/or may be provided externally. Thus, as outlined above, the drive mechanism and the insertion device preferably are operable by hand. Consequently, the actuator may be or may comprise a device or a combination of devices which are adapted to transform a force exerted by hand into a motion of the insertion needle holder, specifically a motion in the longitudinal direction or vice versa. Consequently, the actuator may comprise a mechanical actuator.

The actuator comprises at least one actuator arm, which is pivotable about the at least one axle, in order to actuate the drive mechanism. Specifically, the insertion device may comprise two actuator arms. As used herein, an "actuator arm", also referred to as an actuator lever or simply as a lever, is a movable component, specifically a pivotable component, which may be actuated by a user, preferably by hand, in order to actuate the drive mechanism and/or the insertion device. The term "pivot" generally refers to a movement including at least one rotational movement about at least one rotational axis or axle. Additionally, at least one translational movement may optionally be comprised. However, a purely rotational movement is favorable. Thus, the actuator arm may be arranged pivotably about at least one axle, such that the actuator arm may be pivoted or turned about an axle, preferably by hand, thereby actuating the actuator. In case two actuator arms are provided, both actuator arms may be pivotable about the same axle, or, alternatively, a first one of the actuator arms may be pivotable about a first axle and a second one of the actuator arms may be pivotable about a second axle, wherein the first axle and the second axle may be different.

The insertion device further comprises at least one protection against reuse including at least one locking mechanism. The locking mechanism is adapted to at least partially prevent a back-pivoting of the actuator arm in a direction reversing the actuation direction once the actuator arm has been pivoted by at least one threshold angle. As used herein, a "protection against reuse" generally is one or more of a function, a device, a component or a combination of components adapted for preventing or at least partially preventing a reuse of the insertion device or an insertion needle comprised within the insertion device after full or partial use for insertion and/or after full or partial firing or insertion movement, or at least adapted for rendering the reuse of the insertion device or the insertion needle less probable or more difficult as compared to a situation without protection against reuse.

As further used herein, the term "back-pivoting" refers to a pivoting of the at least one actuator arm in a backward direction, i.e. in a direction opposite an actuation direction. Thus, as an example, the at least one actuator arm may be pivotable in an actuation direction, which may be a linear direction or an angular direction or a direction of rotation, in order to actuate the drive mechanism. The direction or angular direction opposite the actuation direction may be defined as a backward direction, and a pivoting in the backward direction may be defined as a back-pivoting.

The at least one actuator arm, during rotation or pivoting about the at least one axle, rotates about an angle. The angle may be defined by a zero position or initial position of the at least one actuator arm or by any arbitrary coordinate system for defining rotational angles. During pivoting of the at least one actuator arm, the angle is decreased or increased, depending on the definition of the rotational direction. Out of the potential angles which may be reached during pivoting, one, two or more than two threshold angles are defined by the locking mechanism. As used herein, a "threshold angle" generally is an angle defined by the locking mechanism wherein, once the threshold angle has been reached during pivoting, a back pivoting is prevented. Consequently, the term "at least partially prevent a back-pivoting of the actuator arm in a direction reversing the actuation direction once the actuator arm has been pivoted by at least one threshold angle" thus generally refers to the fact that the at least one actuator arm may be pivoted, thereby increasing or decreasing the angle, until the at least one threshold angle has been reached, wherein, as soon as the threshold angle has been reached, a back-pivoting at least partially is prevented. In this regard, the term "at least partially" generally refers to the fact that some tolerances of back-pivoting may occur, such that a back-pivoting may still be possible within given ranges of tolerance, such as by no more than 5°. These tolerances may be defined by mechanical tolerances of the locking mechanism. A forward pivoting of the at least one actuator arm, once the at least one threshold angle or one or more out of a plurality of threshold angles have been reached, may still be possible. Thus, the at least one threshold angle may differ from a final angle, and the at least one actuator arm may still be pivotable in a forward direction, whereas a backward movement is prevented, once the at least one threshold angle has been reached. Specifically, the at least one threshold angle may be or may comprise at least one intermediate angle in between an initial angle of the at least one actuator arm, before actuation, and an end angle which is reached by the at least one actuator arm after full actuation.

In case two actuator arms are provided, one of the actuator arms or each of the actuator arms may be designed in the above-mentioned way. Thus, each actuator arm may be pivoted by a respective angle. Thus, a first actuator arm may be pivoted by a first angle, and a second actuator arm may be pivoted by a second angle. For each of the angles, one, two or more than two threshold angles may be defined. Thus, for each of the actuator arms, a back-pivoting may fully or partially be prevented by the locking mechanism once their respective threshold angles have been reached. Preferably, the two actuator arms are adapted to be pivoted in opposite directions, such that the first angle decreases and the second angle increases.

The insertion device according to the present invention implies a plurality of advantages over the prior art and addresses several technical challenges of known devices. Thus, contrary to the proposed locking mechanism, EP 2 174 680 A1 discloses a protection against reuse, only, which only prevents a reuse of the actuator after full actuation. This setup, however, may still imply the risk of back-pivoting during actuation, i.e. before the end position of the actuator arms is reached. By providing a threshold angle, however, as proposed by the present invention, this risk is reduced.

US 2009/099521 A1 fails to recognize the advantages of using at least one actuator arm. Even though a lever 211 is used, the lever itself is not part of an actuator which actuates a driving mechanism, as disclosed e.g. in paragraph [0068] of this document. Further, no mechanism adapted for preventing a back-pivoting of an actuator arm is disclosed. Instead, a different kind of mechanism is described, in which, once the needle is extended, the needle holder and the driving unit are separated. Consequently, US 2009/099521 A1 fails to recognize the advantages of using an actuator arm being pivotable about at least one axle in order to actuate a drive mechanism, and a locking mechanism being adapted to at least partially prevent a back-pivoting of an actuator arm. This mechanism, however, as proposed by the present invention, provides the advantages of an easy and comfortable insertion, in combination with a reduced risk of misuse or insertion failure by repeated actuation of the actuator.

As outlined above, the at least one threshold angle may contain one, two, three or more than three threshold angles. Specifically, the locking mechanism may define at least two, preferably at least three, threshold angles. These threshold angles specifically may be defined by appropriate mechanical thresholds such as ratchets, hooks, catches or similar mechanical unidirectional devices which, once engaged, prevent a backward movement. Exemplary embodiments will be given in further detail below.

The threshold angles specifically may define locking positions. As used herein, a locking position generally refers to a position of the actuator arm, such as a rotational position, in which the actuator arm precisely or within mechanical tolerances has reached the threshold angle and in which a back-pivoting is prevented. Thus, a locking position may correspond to a position in which the actuator arm has reached a threshold angle. Correspondingly, one locking position per threshold angle may be provided.

The locking mechanism may provide one or preferably at least two locking positions, wherein the actuator arm may be locked in the at least two locking positions. The locking positions may induce several functions. Thus, each locking position may fulfill one or more purposes within a cycle of operation of the insertion device or within an insertion process. Thus, as an example, during the insertion process, the at least one actuator arm or the two actuator arms may be pivoted from an initial position into a final position. During that pivoting, as will be outlined in further detail below, the insertion needle may, during a forward movement, perforate the skin and may introduce the analyte sensor into the body tissue, and may subsequently, during a backward movement, be retracted from the body tissue, leaving the analyte sensor in the body tissue. Both movements may be induced during one total movement of the one or two actuator arms, from their respective initial positions into their respective final positions. During that operation, several locking positions may be reached subsequently by the actuator arms. Thus, the locking positions may comprise an initial locking position in which the actuator arm may be locked after initial activation and an end locking position in which the actuator arm may be locked after full actuation of the actuator. The locking positions may further comprise at least one intermediate locking position in between the initial locking position and the end locking position.

As outlined above, the locking mechanism may be realized in various ways, in order to prevent a back pivoting of the at least one actuator arm. Thus, the locking mechanism may comprise at least one element selected from the group consisting of a catch, a latch, a hook, a pawl, a ratchet. Other embodiments or combinations of the named possibilities are feasible.

As outlined above, the actuator specifically may be adapted to be actuated manually. Thus, the actuator arms may be embodied as lever arms, in order to provide the force necessary for perforation of the skin and insertion of the analyte sensor into the body tissue manually, without the need of further energy reservoirs such as springs.

The actuator, as outlined above, may comprise a first actuator arm pivotable in a first actuation direction and a second actuator arm pivotable in a second actuation direction. The first actuation direction may oppose the second actuation direction. Thus, the first actuator arm may be pivoted in a clockwise direction, and the second actuator arm may be pivoted in a counter-clockwise direction, or vice versa. The first actuator arm and the second actuator arm are pivotable about the same axle or about different axles. The actuator arms may comprise ends, such as free ends, which may be engaged by a user during manual operation of these actuator arms. The ends of the first actuator arm and the second actuator arm may be adapted to approach each other during actuation of the actuator. The ends of the first and second actuator arms may be adapted to be pressed by hand in order to pivot the actuator arms.

In case first and second actuator arms are provided, the first actuator arm may comprise at least one first locking part of the locking mechanism and the second actuator arm may comprise at least one second locking part of the locking mechanism. The first locking part and the second locking part may be adapted to engage once the first and second actuator arms have been pivoted by at least one threshold angle. As used herein, the term "locking part" generally refers to a component of the locking mechanism which, with one or more other components, provides the function of the locking mechanism. Thus, generally, first and second locking parts may be used which interact in order to provide the function of the locking mechanism. Specifically, the locking mechanism may comprise a ratchet or ratchet mechanism. Thus, the first locking part and/or the second locking part may form at least one ratchet mechanism, such as a ratchet mechanism with at least one ratchet pawl. The first locking part and the second locking part specifically may comprise flexible locking parts, in order to provide a flexible locking mechanism, such as a snap in locking mechanism including flexible components such as flexible arms. Thus, generally the locking mechanism may fully or partially be made of a plastic material, specifically a flexible plastic material. Specifically, the first locking part and the second locking part may comprise elements which at least partially are made of a plastic material.

Further embodiments which will also be outlined in further detail below refer to the drive mechanism. Specifically, the drive mechanism may comprise a rotor adapted to transform an actuation motion of the actuator into a motion of the needle holder in the longitudinal direction. It shall be noted, however, that other types of drive mechanisms are generally feasible, even though the use of a rotor is favorable in various ways. The actuator may be adapted to be actuated in at least one actuation direction, preferably at least one actuation direction deviating from the longitudinal direction.

The insertion device may further comprise at least one protection against unwanted use. Specifically, the insertion device may comprise at least one safety lock. The safety lock, in a locked position, may be adapted to at least partially block a rotation of the rotor and, in an unlocked position, may be adapted to permit the rotation of the rotor. The safety lock, in an embodiment, may comprise one or more operation elements such as at least one a slide switch. As will be outlined in further detail below, the safety lock may comprise an abutment portion, wherein the abutment portion, in the locked position, may be adapted to abut on a rotor of the drive mechanism, thereby at least partially preventing the rotation of the rotor. In the unlocked position, the abutment portion may be moved away from the rotor and may permit the rotation of the rotor.

As outlined above, the actuator specifically may be adapted to be actuated manually. The actuator may be adapted to drive the drive mechanism, preferably the rotor, via at least one gearing mechanism. Exemplary embodiments of the gearing mechanism will be given in further detail below.

As outlined above, the at least one actuator may be adapted to be actuated in at least one actuation direction. In case a plurality of actuators is provided, each actuator may have its own actuation direction. Thus, as an example, in case two actuator arms are provided, each actuator arm may be adapted to be actuated in a corresponding actuation direction, such that, in total, the at least one actuation direction comprises a first actuation direction for a first actuator arm and a second actuation direction for a second actuator arm. The at least one actuation direction may deviate from the longitudinal direction. As used herein, an actuation direction generally refers to a direction in space or a combination of a plurality of directions in space in which a force, specifically a mechanical force, may be applied to the actuator, thereby initiating an actuation of the drive mechanism by the actuator. The actuation direction may be a single linear direction or may be a combination of a plurality of different directions, such as directions on a curved actuation path.

The at least one actuation direction may deviate from the longitudinal direction. Thus, an actuation of the actuator by an external force, such as by manually actuating the actuator, evokes a force and/or a motion of the actuator in a direction deviating from the longitudinal direction. Thus, as an example, the actuation direction may be perpendicular to the longitudinal direction, such as in an angular region of 90°±80°, 90°±70° or 90°±60°. Further, during actuation of the actuator, the actuation direction may change since the actuator moves, such as on a predetermined path of movement. The actuation direction thus may deviate from the longitudinal direction specifically at all times during actuation of the actuator. Other embodiments are feasible.

In order to transform a motion of the actuator into a motion of the insertion needle holder in the longitudinal direction, specifically in order to transform the actuation in the actuation direction into a drive motion of the insertion needle holder in the longitudinal direction, the drive mechanism, as outlined above, may comprise at least one rotor. As used herein, a rotor is a mechanical component which is pivotable about at least one axis or axle. Specifically, the rotor may be adapted to be rotated or pivoted about the axis or axle and may be adapted to eccentrically engage with at least one further element, such as with at least one plunger or push rod of the drive mechanism. Specifically, the rotor may be or may comprise an eccentric disc which is pivotable about at least one eccentric axis or axle. As will be outlined in further detail below, the rotor itself may be composed of a single element or may be composed of a plurality of rotor parts which may be connected to one another in a fixed fashion or which may be connected such that the rotor parts may pivot about one another.

The rotor may be adapted to transform an actuation motion of the actuator into a motion of the needle holder in the longitudinal direction. Thus, as outlined above, the rotor may interact with one or more further components of the drive mechanism, such as with at least one plunger and/or push rod which directly or indirectly drive the insertion needle holder in the longitudinal direction and optionally in a reverse direction.

As discussed above, in an embodiment, the insertion device may comprise at least one safety lock. As used herein, a safety lock generally refers to a device or combination of devices adapted for performing at least one safety function. Specifically, the safety lock may be adapted for preventing an unwanted actuation of the insertion device, thereby preventing an unwanted driving of the insertion needle holder and/or the insertion needle. Thus, as an example, the insertion needle holder may be supported within a casing of the insertion device in a movable fashion, such as by providing one or more bearings or one or more guides, such as one or more guide rails or slides. Specifically, the insertion needle holder may be stored or guided in a linearly movable fashion within the casing of the insertion device. The insertion needle holder may have a retracted position or a rest position, in which the insertion needle holder is stored before insertion and in which the insertion needle does not protrude from the insertion device.

The safety lock may be adapted to prevent the insertion needle holder from unwantedly leaving the rest position or a storage position and/or may be adapted to generally prevent an unwanted firing of the insertion device. As used herein, a "firing" may refer to an actuation of the actuation device and/or a process of forward movement of the insertion needle holder and/or the insertion needle. The safety lock may comprise at least one locked position and at least one unlocked position, wherein in the locked position, an unwanted firing may be locked, and wherein in the unlocked position, a firing of the insertion device and, thus, an insertion of the analyte sensor into the body tissue, is enabled.

The safety lock, in a locked position, may be adapted to at least partially block a rotation of the rotor. As used herein, the term "at least partially block" refers to the fact that the safety lock fully prevents a rotation of the rotor and, thus, prevents any rotation about an arbitrary angle or, alternatively, prevents a rotation about an angle which is greater than a threshold angle or tolerance angle. Thus, as an example, the tolerance angle may be an angle which will not lead to a significant motion of the needle holder, such as a motion of less than 3 mm, preferably of less than 2 mm or less than 1 mm. Thus, generally, the term "at least partially block" refers to a total blocking of the rotation of the rotor or a blocking of the rotation of the rotor, within given ranges of tolerance. In an unlocked position, the safety lock is adapted to permit the rotation of the rotor.

The safety lock may comprise one or more blocking elements which abut on the rotor in the locked position. The one or more blocking elements may be movable and may, in the locked position, directly or indirectly abut on the rotor or a part thereof in order to prevent a rotation of the rotor. In the unlocked position, the one or more blocking elements may be moved out of the way of the rotor in order to free the rotor and in order to permit the rotation of the rotor as soon as the drive mechanism is actuated by the actuator.

The safety lock preferably may be operable by hand. Thus, the safety lock may comprise at least one operation element such as at least one switch. As will be outlined in further detail below, the operation element preferably may comprise at least one slide switch. However, other types of switches are feasible. As used herein, an operation element generally refers to an element which may be operated by a user of the insertion device in order to transfer the safety lock from the locked position into the unlocked position or preferably by hand.

The operation element, such as the at least one switch, preferably may be marked optically, such as by a specific color distinguishing the operating element from the remaining casing. Thus, as an example, the operation element may have a different color than a casing of the insertion device in an area around the operation element. Thus, as an example, the slide switch may comprise a blue color, whereas the casing of the insertion device may have a white color. Other types of colors are feasible.

As outlined above, the safety lock specifically may comprise a slide switch. The slide switch may be slidable and may be connected to the above-mentioned blocking element or locking element of the safety lock which locks or unlocks the at least one rotor. Thus, as an example, the slide switch may be connected, via one or more rods or rigid elements, with the at least one blocking or locking element of the safety lock. Specifically, the slide switch may be linearly slidable in a backward direction, which may also be referred to as a rearward direction. As defined herein, a forward motion of the needle holder during insertion of the analyte sensor, i.e. a motion towards the skin during penetrating the skin, may be defined as a forward direction, and the rearward direction or backward direction may be a direction opposite the forward direction. The slide switch may be slidable in the backward direction during unlocking the safety lock. This slidability in the rearward direction ensures that an unwanted unlocking may not take place during placement of the insertion device onto the skin of the user.

As outlined above, the safety lock may comprise a locking element, which may also be referred to as a blocking element. Specifically, the safety lock may comprise an abutment portion, which may be part of the locking or blocking element. The abutment portion, in the locked position, may be adapted to abut on the rotor, thereby at least partially preventing the rotation of the rotor. In the unlocked position, the abutment portion may be moved away from the rotor and may permit the rotation of the rotor. Thus, the abutment portion may be part of the locking element.

In addition or as an alternative to using a slide switch, the safety lock may also comprise at least one pin which fulfills the above-mentioned function of fully or partially blocking a rotation of the rotor in a locked position and, in an unlocked position, permitting the rotation of the rotor. Therein, the pin may function as a locking or blocking element of the safety lock and, simultaneously, as an operation element of the safety lock. Thus, by removing the pin, such as manually, the rotation of the rotor may be freed. The locked position, thus, may be a position in which the pin is inserted into the insertion device, specifically into a casing of the insertion device, and the unlocked position may be a position in which the pin is removed from the insertion device, specifically from the casing of the insertion device.

As used herein, a pin generally refers to an arbitrary element having an elongated portion, such as a cylindrical portion, specifically a rigid elongated portion. The pin, specifically the elongated portion, may have a cylindrical shape having an arbitrary cross-section, such as a circular cross-section, an oval cross-section or a polygonal cross-section. The pin, as an example, may fully or partially be made of a metal and/or a plastic material. Other materials are feasible. The pin, in addition to the elongated portion, may also comprise a handling portion, such as a widened portion which specifically may be or may comprise a knob. The handling portion, specifically, may have a wider diameter or equivalent diameter as compared to the elongated portion. The handling portion specifically may be located outside a casing of the insertion device and may be adapted for being grasped by a user in order to pull the pin out of the casing, thereby moving the safety lock from the locked position into the unlocked position.

The pin generally may interact with the rotor in an arbitrary way. Specifically, the rotor, such as one or more rotor parts, may comprise at least one opening which may be engaged by the pin in the locked position. Thus, as used herein, an opening generally refers to an open space, such as a bore, a hole, a notch or any other type of opening fully or partially surrounded by material of the rotor, which may be engaged by the pin.

In the locked position, the pin specifically may be inserted into the at least one opening in the rotor and may be adapted to at least partially block the rotation of the rotor.

The pin may be manually removable in order to bring the safety lock in the unlocked position. In the unlocked position and with the pin removed, the rotation of the rotor may be permitted.

The pin specifically may extend through a casing of the insertion device into an interior of the casing. Thus, the casing may provide one or more holes or bores, such as in a front surface and/or in a back surface, and the at least one hole or bore into the interior of the casing. The pin may be adapted to be removed by pulling out the pin from the casing. The pin may further extend through the one or more actuator arms in the locked position.

The use of a pin generally implies a plurality of advantages. Thus, besides providing the functionality of the safety lock, the pin may further act as an assembling aid during assembly of the insertion device. The pin may be inserted into the casing, such as by sticking the pin through the at least one hole or bore into the interior of the casing, and components of the insertion device may subsequently be mounted onto the pin and may be held in place by the pin. Before use of the insertion aid, the pin may be removed, thereby freeing the components and allowing for a movement of the components in the casing, such as a rotation of the rotor and/or a movement of the at least one actuator. Additionally or alternatively, the pin may act as a transport lock and may prevent an unwanted actuation of the insertion device during transport and/or storage of the insertion device.

The actuator, as outlined above, specifically may be adapted to be actuated manually. Thus, as outlined above, the actuator specifically may comprise at least one arm and/or at least one lever which may be actuated manually. As an example and as will be outlined in further detail below, the actuator may comprise one or two arms or levers which, in a non-actuated state of the insertion device, may protrude from a casing of the insertion device and which may be tilted and/or pushed by hand. As an example, the insertion device may comprise two arms or levers which protrude on both sides of the casing and which may be pushed inwardly, thereby tilting the arms or levers about one or two axes, thereby actuating the actuator.

The actuator specifically, as outlined above, may comprise at least one actuator arm which may be pivoted manually, preferably at least one lever. The actuator arm specifically may be pivotable about at least one axle. Specifically, the actuator may comprise two actuator arms which may be pivoted such that end points of the arms approach during pivoting. In other words, the actuator arms, which may also be referred to as levers, may be pushed inwardly, thereby pivoting the actuator arms in opposite directions. The actuator arms specifically may be pivotable about one and the same axle. However, other actuators are feasible, such as actuators having separate axels for the actuators.

The actuator specifically may be adapted to drive the rotor via at least one gearing mechanism. Thus, as an example, the drive mechanism may comprise at least one pinion which is connected with the rotor. As an example, the pinion may be part of the rotor and/or may be connected to the rotor such that a rotation of the pinion drives a rotation of the rotor. The pinion may be part of the gearing mechanism. The pinion may be driven by the at least one actuator arm, such as by the two actuator arms, specifically by a toothed rack. Thus, the pinion may interact with at least one toothed rack connected to the at least one actuator. Thus, generally, the gearing mechanism may comprise at least one toothed rack connected to the at least one actuator, such as to the at least one actuator arm. In case two actuator arms or levers are present, each of the actuator arms may comprise a toothed rack interacting with the pinion. Thus, a pivoting of the at least one actuator arm may drive a rotation of the pinion and, thereby, may drive a rotation of the rotor.

The drive mechanism, as outlined above, may further comprise a plunger, which may also be referred to as a piston, a piston rod or a push rod, wherein the rotor may be adapted to drive the needle holder in the longitudinal direction via the at least one plunger.

The insertion device, as outlined above, may further comprise at least one insertion needle. The insertion needle specifically may be coupled to the insertion needle holder such that the insertion needle holder is adapted to drive the insertion needle in the longitudinal direction in order to penetrate a skin portion.

In a further aspect of the present invention, an insertion kit for inserting an analyte sensor into a body tissue of a user is disclosed. As used herein, an "insertion kit" generally refers to a combination of components serving the purpose of inserting the analyte sensor into the body tissue, wherein the components may be handled independently or in combination. The insertion kit comprises an insertion device according to the present invention, such as according to any one of the embodiments listed above or listed in further detail below. The insertion kit further comprises at least one analyte sensor. In a ready-to-use state, the analyte sensor may fully or partially be inserted into the insertion needle and/or into the insertion device, in order to be implanted into the body tissue. As outlined above, the analyte sensor specifically may be an electrochemical analyte sensor, preferably for detecting one or more analytes which may take part in the metabolism, such as one or more analytes selected from the group consisting of glucose, cholesterol, triglycerides or lactate. Other analytes and/or combinations of analytes are feasible.

The insertion kit further may comprise at least one body patch adapted for attachment to a skin surface, such as to a skin surface of a user and/or a patient. In order to be attached to the skin surface, the body patch specifically may comprise one or more adhesives, such as one or more adhesive patches and/or plasters and/or other types of attachment elements for attachment of the body patch to the skin surface.

The body patch may be adapted to be coupled to the insertion device during inserting the analyte sensor into the body tissue. Thus, the body patch may contain one or more receptacles adapted for receiving a portion of the analyte sensor and for holding the analyte sensor. Thus, in an inserted state, a portion of the analyte sensor may be held by the body patch, such as in one or more receptacles and/or plugs. Another portion, which may also be referred to as an implantable portion, may transcutaneously be inserted into the body tissue, such that the analyte sensor protrudes from the body patch, disposed on an outer surface of the skin, through the skin into the body tissue.

The insertion device may be adapted to push the analyte sensor into the body patch during insertion. Thus, as an example, the analyte sensor may provide a sensor plug or sensor connector which is pushed into a receptacle of the body patch during insertion and which, thereby, is mechanically fixed or mounted within the body patch, whereas a portion of the analyte sensor transcutaneously protrudes into the tissue.

The body patch further may be adapted to be decoupled from the insertion device after insertion. As an example, the insertion device may provide a locking mechanism, which may also be actuated by the actuator and which may be adapted for holding the body patch during insertion and for releasing the body patch after insertion. Thus, as an example, during insertion, such as during pulling back the insertion needle from the body tissue, the body patch may be decoupled from the insertion device. Thereby, the body patch, with a part of the analyte sensor coupled to the body patch, may remain on the skin surface of the user, with a part of the analyte sensor protruding from the body patch into the body tissue, and the insertion device may be released from the body patch. Thus, as outlined above, the analyte sensor may comprise at least one mounting part, such as at least one connector or plug, which remains within the body patch. The insertion kit may be adapted to couple the mounting part to the body patch during insertion, such as by pushing the mounting part into an appropriate receptacle within the body patch. The coupling of the mounting part to the body patch specifically may be performed and/or enabled by the above-mentioned actuator and/or by the above-mentioned drive mechanism. Thus, a push rod and/or plunger, such as the same push rod or plunger which is used for driving the needle holder, may also enable a mounting of the mounting part to the body patch, such as by pushing the mounting part into an appropriate receptacle, such as a receptacle having a catch or lock, of the body part.

In a further aspect of the present invention, a method for inserting an analyte sensor into a body tissue is disclosed. The method comprises using the insertion device according to the present invention, such as the insertion device according to one or more of the embodiments disclosed above or disclosed in further detail below. The method may comprise actuating the actuator for driving the insertion needle holder and for initiating an insertion of the analyte sensor. The method may further comprise additional method steps.

The insertion device, the insertion kit and the method for inserting the analyte sensor into the body tissue provide a large number of advantages over known devices and methods. Thus, the safety lock and/or the operation element, such as the slide switch, may be designed in a robust and simple way, and may be adapted for use even by elderly people, children or handicapped people. Further, due to the locking mechanism, a reuse of the insertion device of the full or partial first use may efficiently be prevented. Thus, as outlined above, by using the locking mechanism, and unwanted backward movement of the drive mechanism may be prevented.

The locking mechanism may be implemented in a safe and simple way, such as by using the above-mentioned elements. Specifically, by using a ratchet-type mechanism, a simple and efficient protection against reuse may be implemented. As an example, the locking mechanism may comprise two points or more of no return, corresponding to the above-mentioned locking positions, wherein each point of no return, once reached during actuation, denotes a point after which no back-pivoting of the actuator arms is possible.

The above-mentioned at least two locking positions may, as outlined above, serve several functions. Thus, as an example, one locking position or point of no return out of the at least two locking positions may correspond to a state in which the insertion needle is extended farthermost from the insertion device, such as into the body tissue. Thereby, this locking position may prevent that, by reusing the actuator, the drive mechanism and the insertion needle may, again, hit the sensor and may destroy the sensor. A second or further locking position or point of no return out of the at least two locking positions may correspond to a state in which the inserter automatically decouples from the body patch. By this locking position, it may be prevented that, after decoupling the inserter from the body patch, the insertion needle is, again, extended from the inserter. The second locking position thus may prevent that, in a used state, the insertion needle is accessible from the outside of a casing of the insertion device and, thus, may prevent injuries induced by the contaminated insertion needle. A further locking position or point of no return may be a position in which the actuator is in an end position, such as a position in which the at least one actuator arm or the actuator arms are fully pivoted. This locking position, which may also be referred to as the final locking position or end locking position, may keep the actuator arm or actuator arms in a final state, such as in predetermined grooves or depressions within the casing.

Thus, as an example, the at least two locking positions or points of no return may comprise at least two locking positions or points of no return selected from the group consisting of:
1. an initial locking position or point of no return, in which the at least one actuator arm may be locked after initial activation,
2. an end locking position or point of no return in which the actuator arm may be locked after full actuation of the actuator,
3. an intermediate locking position or point of no return, corresponding to a state in which the insertion needle is extended farthermost from the insertion device,
4. an intermediate locking position or point of no return, corresponding to a state in which the inserter automatically decouples from the body patch.

These locking positions may be combined in an arbitrary way, such as by providing one of the following combinations of locking positions or points of no return: 1 and 2; 1 and 3; 1 and 4; 2 and 3; 2 and 4; 3 and 4; 1, 2 and 3; 1, 2 and 4; 2, 3 and 4; 1, 2, 3 and 4. Further, one or more of these locking positions or points of no return may be combined with one or more further locking positions or points of no return. It shall be noted that the above-mentioned locking positions are examples of helpful and advantageous locking positions which provide good and valuable protection against reuse, destruction and injuries, for the reasons given above. Still, other locking positions or points of no returns may be used.

As outlined above, the actual insertion process may be initiated by pressing the at least one actuator arm, preferably the actuator arms, together. By the drive mechanism, such as by transforming a motion of the actuator arms via a rotational movement of the rotator into a linear movement, the insertion needle with the analyte sensor disposed therein may be driven. Thereby, the analyte sensor may transcutaneously be inserted into the body tissue. Once the analyte sensor is inserted and once a sensor connector is transferred to the body patch, the insertion needle may be pulled back. The insertion needle may be retracted into the casing of the inserter and may be secured within the casing of the insertion device. The body patch may be decoupled from the inserter.

The drive mechanism, as outlined above, may simply comprise a gear transmission or gearing. Still, additionally or alternatively, the drive mechanism may comprise other types of drives, such as one or more of a belt drive, a friction gear, a spindle drive, a spindle-top drive or combinations thereof. Other types of drive mechanisms are feasible. The actuator may be operable at a minimum force. The user simply has to apply sufficient force for actually transferring the insertion needle, such as the cannula, through the skin into the body tissue. An over-dimensioning of the drive mechanism, as in the case of known insertion devices, is not necessary. For inserting the insertion needle into the skin, for retracting the insertion needle and for decoupling the insertion device from the body patch, only one handling step is required, as opposed to the plurality of handling steps required in known devices. Thus, generally, the actuator and the drive mechanism in the present insertion device may be designed such that a forward movement of the insertion needle, a coupling of the connector of the analyte sensor to the body patch, a retraction of the insertion needle from the body tissue and a decoupling of the insertion device from the body patch may be performed during one smooth actuation movement of the actuator arm or actuator arms, i.e. during one actuation process.

The insertion may take place in a guided movement. Thus, by an appropriate design of the actuator and the drive mechanism, all parts of the drive mechanism and the insertion needle holder may be guided. A ballistic movement may be avoided. Consequently, the noise during insertion may significantly be reduced as compared to ballistic inserters. A subjective feeling of pain in use by noise may thus be reduced.

Further, a single-handed actuation of the actuator mechanism may be feasible. The actuation of the actuator by the actuator arms may take place in an actuation direction deviating from the puncture direction all longitudinal direction. This transformation may further include a psychological advantage over devices in which the user actually has to actuate the insertion device against his or her own body, since the latter implies a further psychological effort.

The locking mechanism may provide a safe and simple failsafe function. Thus, in order to prevent a reuse after full or partial operation of the actuator, the one, two or more locking positions may be provided. Specifically, by using these locking positions, the user may be prevented from accidentally or out of play instinct actuating the actuator and reusing the insertion device. Further, an intermediate return of the actuation movement may be prevented. Thereby, injuries or distraction of the insertion device or of the analyte sensor may efficiently be prevented.

Further, by the above-mentioned optional safety lock, a safe measure against misuse and/or faulty operation may be provided. An unwanted or incidental initiation of the insertion process may be prevented, since the user deliberately has to operate the safety lock, such as the slide switch. The safety lock and the remainder of the insertion device may form a unit. Consequently, no additional safety lock has to be disposed of after insertion. Further, the safety lock may be designed to provide the above-mentioned safety mechanism in a non-reversible way. Thus, the safety lock may be adapted such that, after having been brought in the unlocked position, the safety lock may not be brought back into the locked position, by hand or at least without tools. Thus, specifically in case the safety lock comprises an operation element, the operation element may be adapted to be operated by the user in one way only, in order to bring the safety lock from the locked position into the unlocked position. By implementing the safety lock in this non-reversible way, the safety lock may guarantee that the insertion needle has not been used before and, thus, may provide a protection against reuse. The operation element may be designed in a way easy to use, such as by providing haptic feedback to the user. In addition, the operation element may be designed such that the locked or unlocked position is audible or visible, such as by inspecting a position of a slide switch and/or by listening to the clicking noise during unlocking the locking element.

The operation element specifically may be placed in a position of the casing of the insertion element which is easily accessible to the user. Thus, as an example, the operation element such as the slide switch may be deposited on a front side of the casing. Further, the operation element may be placed such that a user may both operate the actuator manually and unlock the safety lock by using the operation element, preferably without changing the grip. Thus, as outlined above, the actuator may comprise two or more actuator arms or actuator levers which may be operated simultaneously with the fingers and the heel of one hand. The operation element may be placed such that it is, during the actuation motion, within reach of the thumb or the forefinger of the hand operating the operation arms. As further outlined above, the operation element such as the slide switch may be operable in an ergonomically simple way. Thus, in case a slide switch is provided, the slide switch may be operable such that, for unlocking the safety lock, the slide switch has to be pushed or pulled into a backward or rearward direction, such as away from the skin of the patient or user. The safety lock further may act as a transportation lock or as a transportation safety device, such as for preventing an unwanted firing of the insertion device during transportation or storage. Thus, an additional transportation locking device may be omitted, thereby reducing the overall number of parts. Still, an additional transportation locking device or transportation safety device may be implemented additionally.

Summarizing the findings of the present invention, the following embodiments are preferred:

Embodiment 1

An insertion device for inserting an analyte sensor into a body tissue, the insertion device comprising an insertion needle holder and a drive mechanism for linearly driving the insertion needle holder in a longitudinal direction, the drive mechanism comprising at least one actuator for actuating the drive mechanism, the actuator comprising at least one actuator arm, wherein the actuator arm is pivotable about at least one axle in order to actuate the drive mechanism, wherein the insertion device comprises at least one protection against reuse including at least one locking mechanism, wherein the locking mechanism is adapted to at least partially prevent a back-pivoting of the actuator arm in a direction reversing the actuation direction once the actuator arm has been pivoted by at least one threshold angle.

Embodiment 2

The insertion device according to the preceding embodiment, wherein the locking mechanism defines at least two, preferably at least three, threshold angles.

Embodiment 3

The insertion device according to any one of the preceding embodiments, wherein the locking mechanism provides at least two locking positions, wherein the actuator arm may be locked in the at least two locking positions.

Embodiment 4

The insertion device according to the preceding embodiment, wherein the locking positions comprise an initial locking position in which the actuator arm may be locked after initial activation and an end locking position in which the actuator arm may be locked after full actuation of the actuator.

Embodiment 5

The insertion device according to the preceding embodiment, wherein the locking positions comprise at least one intermediate locking position in between the initial locking position and the end locking position.

Embodiment 6

The insertion device according to any one of the preceding embodiments, wherein the locking mechanism comprises at least one element selected from the group consisting of a catch, a hook, a latch, a pawl, a ratchet.

Embodiments 7

The insertion device according to any one of the preceding embodiments, wherein the actuator is adapted to be actuated manually.

Embodiment 8

The insertion device according to any one of the preceding embodiments, wherein the actuator comprises a first actuator arm pivotable in a first actuation direction and a second actuator arm pivotable in a second actuation direction, wherein the first actuation direction opposes the second actuation direction.

Embodiment 9

The insertion device according to the preceding embodiment, wherein the first actuator arm and the second actuator arm are pivotable about the same axle.

Embodiment 10

The insertion device according to any one of the two preceding embodiments, wherein ends of the first actuator arm and the second actuator arm are adapted to approach each other during actuation of the actuator.

Embodiment 11

The insertion device according to the preceding embodiment, wherein the ends of the first and second actuator arms are adapted to be pressed by hand in order to pivot the actuator arms.

Embodiment 12

The insertion device according to any one of the four preceding embodiments, wherein the first actuator arm comprises at least one first locking part of the locking mechanism and wherein the second actuator arm comprises at least one second locking part of the locking mechanism, wherein the first locking part and the second locking part are adapted to engage once the first and second actuator arms have been pivoted by the at least one threshold angle.

Embodiment 13

The insertion device according to the preceding embodiment, wherein the first locking part and/or the second part form at least one ratchet mechanism.

Embodiment 14

The insertion device according to any one of the two preceding embodiments, wherein the first locking part and the second locking part comprise flexible locking parts.

Embodiment 15

Insertion device according to any one of the three preceding embodiments, wherein the first locking part and the second locking part comprise elements at least partially made of a plastic material.

Embodiment 16

The insertion device according to any one of the preceding embodiments, wherein the drive mechanism comprises a rotor adapted to transform an actuation motion of the actuator into a motion of the needle holder in the longitudinal direction.

Embodiment 17

The insertion device according to the preceding embodiment, wherein the actuator is adapted to be actuated in at least one actuation direction, preferably at least one actuation direction deviating from the longitudinal direction.

Embodiment 18

The insertion device according to any one of the two preceding embodiments, wherein the insertion device further comprises at least one safety lock, wherein the safety lock, in a locked position, is adapted to at least partially block a rotation of the rotor and wherein the safety lock, in an unlocked position, is adapted to permit the rotation of the rotor.

Embodiment 19

The insertion device according to the preceding embodiment, wherein the safety lock comprises a slide switch.

Embodiment 20

The insertion device according to any one of the two preceding embodiments, wherein the safety lock comprises an abutment portion, wherein the abutment portion, in the locked position, is adapted to abut on a rotor of the drive mechanism, thereby at least partially preventing the rotation of the rotor, wherein, in the unlocked position, the abutment portion is moved away from the rotor and permits the rotation of the rotor.

Embodiment 21

The insertion device according to any one of the three preceding embodiments, wherein the safety lock comprises at least one pin, wherein, in the locked position, the pin is inserted into at least one opening in the rotor and is adapted to at least partially block a rotation of the rotor, wherein the pin is manually removable in order to bring the safety lock in the unlocked position, wherein, in the unlocked position and with the pin removed, the rotation of the rotor is permitted.

Embodiment 22

The insertion device according to the preceding embodiment, wherein the pin extends through a casing of the insertion device into an interior of the casing and is adapted to be removed by pulling out the pin from the casing.

Embodiment 23

The insertion device according to any one of the preceding embodiments, wherein the actuator is adapted to be actuated manually.

Embodiment 24

The insertion device according to any one of the preceding embodiments, wherein the actuator is adapted to drive the drive mechanism, preferably the rotor, via at least one gearing mechanism.

Embodiment 25

An insertion kit for inserting an analyte sensor into a body tissue, comprising at least one insertion device according to any one of the preceding embodiments, further comprising at least one analyte sensor.

Embodiment 26

The insertion kit according to the preceding embodiment, wherein the analyte sensor is an electrochemical analyte sensor, preferably for detecting one or more of the following analytes: glucose, cholesterol, triglycerides, lactate.

Embodiment 27

The insertion kit according to any one of the two preceding embodiments, further comprising at least one body patch adapted for attachment to a skin surface, wherein the body patch is adapted to be coupled to the insertion device during inserting the analyte sensor into the body tissue.

Embodiment 28

The insertion kit according to the preceding embodiment, wherein the body patch is further adapted to be decoupled from the insertion device after insertion.

Embodiment 29

The insertion kit according to any one of the two preceding embodiments, wherein the analyte sensor comprises at least one mounting part, wherein the insertion kit is adapted to couple the mounting part to the body patch during insertion.

Embodiment 30

A method for inserting an analyte sensor into a body tissue, the method comprising using the insertion device according to any one of the preceding embodiments referring to an insertion device.

SHORT DESCRIPTION OF THE FIGURES

Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

DETAILED DESCRIPTION OF THE EMBODIMENTS

Figure 1:
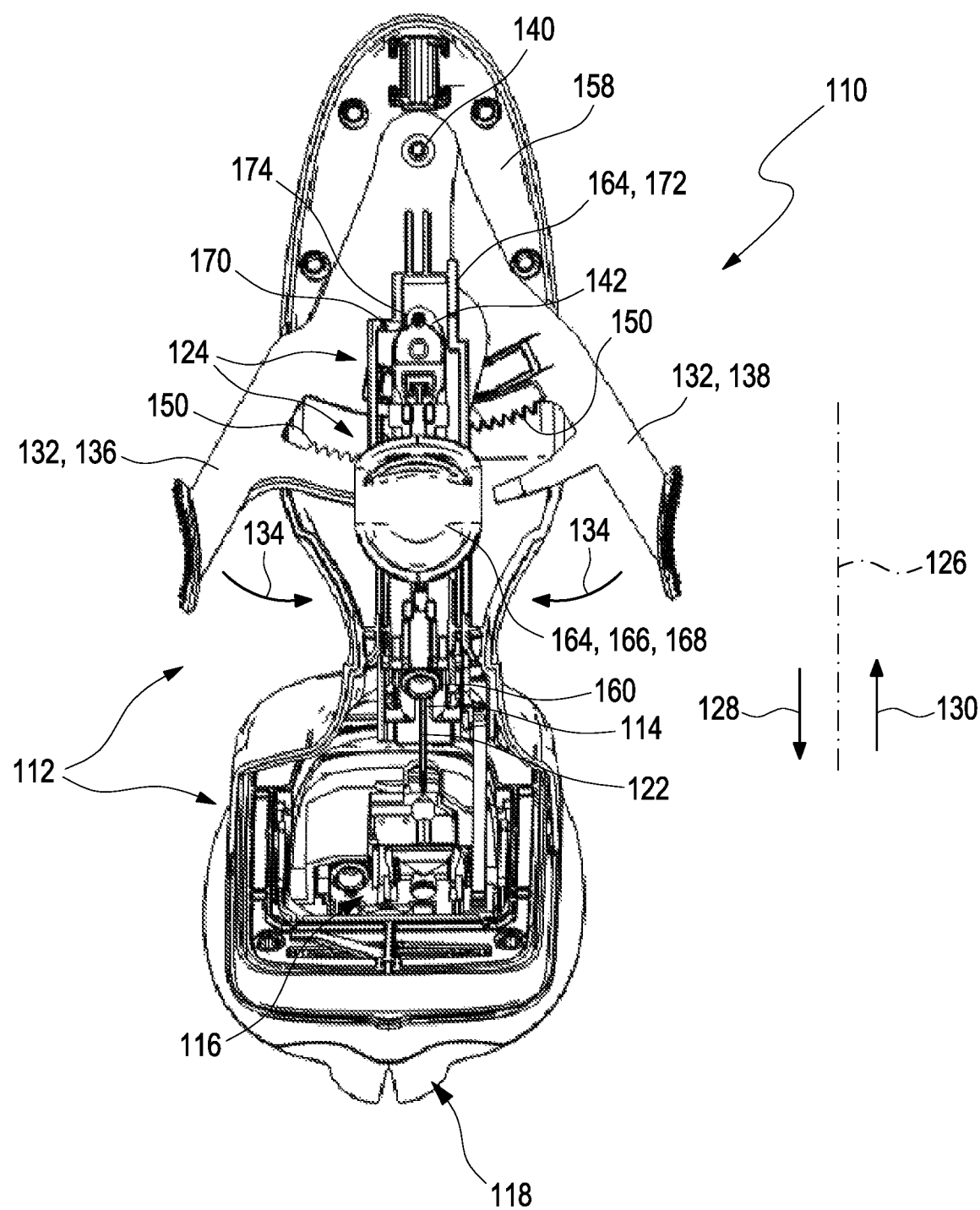
FIG. 1 shows an exemplary embodiment of an insertion device and an insertion kit, in a perspective front view, with a casing of the insertion device partially opened.

In FIGS. 1 to 4, 5A to 5C, and 6 to 8, an exemplary embodiment of an insertion device 110 and an insertion kit 112 is shown in various positions and in various views. The insertion kit 112, besides the insertion device 110, comprises an analyte sensor 114 and a body patch 116 which, in this exemplary embodiment, may be attached to a skin surface e.g. by an adhesive plaster 118. In FIGS. 1 to 4, 5A to 5C, the functionality of the insertion device 110 including an actuation mechanism and a safety lock is disclosed, whereas in FIGS. 6 to 8, a protection against reuse of the insertion device 110 will be explained in further detail. In the following, reference will be made to all Figures.

The insertion device 110, in most details except for the safety lock and the protection against reuse, may correspond to the insertion device as disclosed e.g. in EP 2 174 680 A1 or in WO 2010/072290 A1. Specifically, with regard to details of an actuation mechanism and with regard to details of the overall functionality and body patch, reference may be made to these prior art documents.

Figure 4:
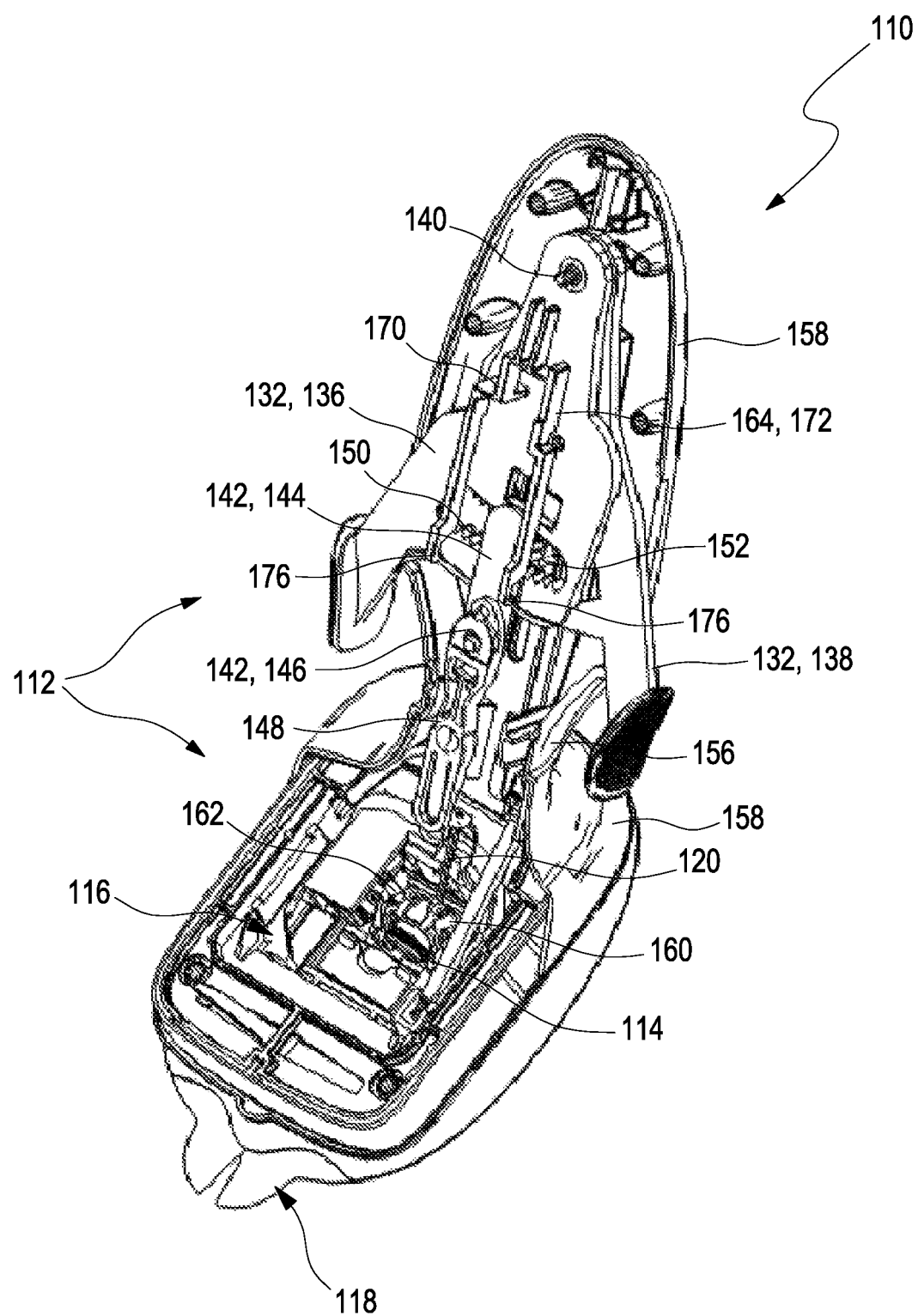
FIG. 4 shows the setup of FIG. 3 with the plunger removed.

The insertion device 110 comprises an insertion needle holder 120 which is visible specifically in FIG. 4. The insertion needle holder 120 is adapted to drive an insertion needle 122 which is mainly visible in FIG. 2. The insertion needle 122, as an example, may be designed as a hollow needle or cannula and is adapted for receiving the analyte sensor 114 during insertion into the body tissue.

The insertion device further comprises a drive mechanism 124 adapted for driving the insertion needle holder 120 in a longitudinal direction. The longitudinal direction, which is symbolically depicted by dash line 126 in FIG. 1, may be defined as a longitudinal axis parallel to a puncture motion during insertion of the analyte sensor 114, i.e. as an axis along which the insertion needle 122 moves during the puncture motion. Therein, a direction of incision, i.e. a downward direction in FIG. 1, may be defined as a forward direction 128, whereas an opposite direction may be defined as a rearward direction 130 or backward direction.

The drive mechanism 124 comprises an actuator 132. The actuator 132 specifically may be adapted to be actuated in at least one actuation direction 134, wherein the actuation direction 134 specifically may deviate from the longitudinal direction. In the exemplary embodiment of FIG. 1, corresponding to the actuation mechanisms of documents EP 2 174 680 A1 or WO 2010/072290 A1, the actuator 132 comprises two opposite actuator arms 136, 138 which may also be referred to as actuator levers, which are pivotable. In the exemplary embodiment shown in the Figures, as an example, the actuator arms 136, 138 may be pivotable about a common axle 140.

The actuator arms 136, 138 are adapted to be pushed, during actuation, such as in the actuation directions 134, i.e. inwardly in FIG. 1. The drive mechanism 124 further comprises at least one rotor 142. The rotor 142 in the exemplary embodiment shown in the Figures, is a multiple-part rotor 142 and comprises a first rotor part 144 and a second rotor part 146, wherein the latter may already be considered as part of a plunger 148 connected to the rotor 142.

Figure 2:
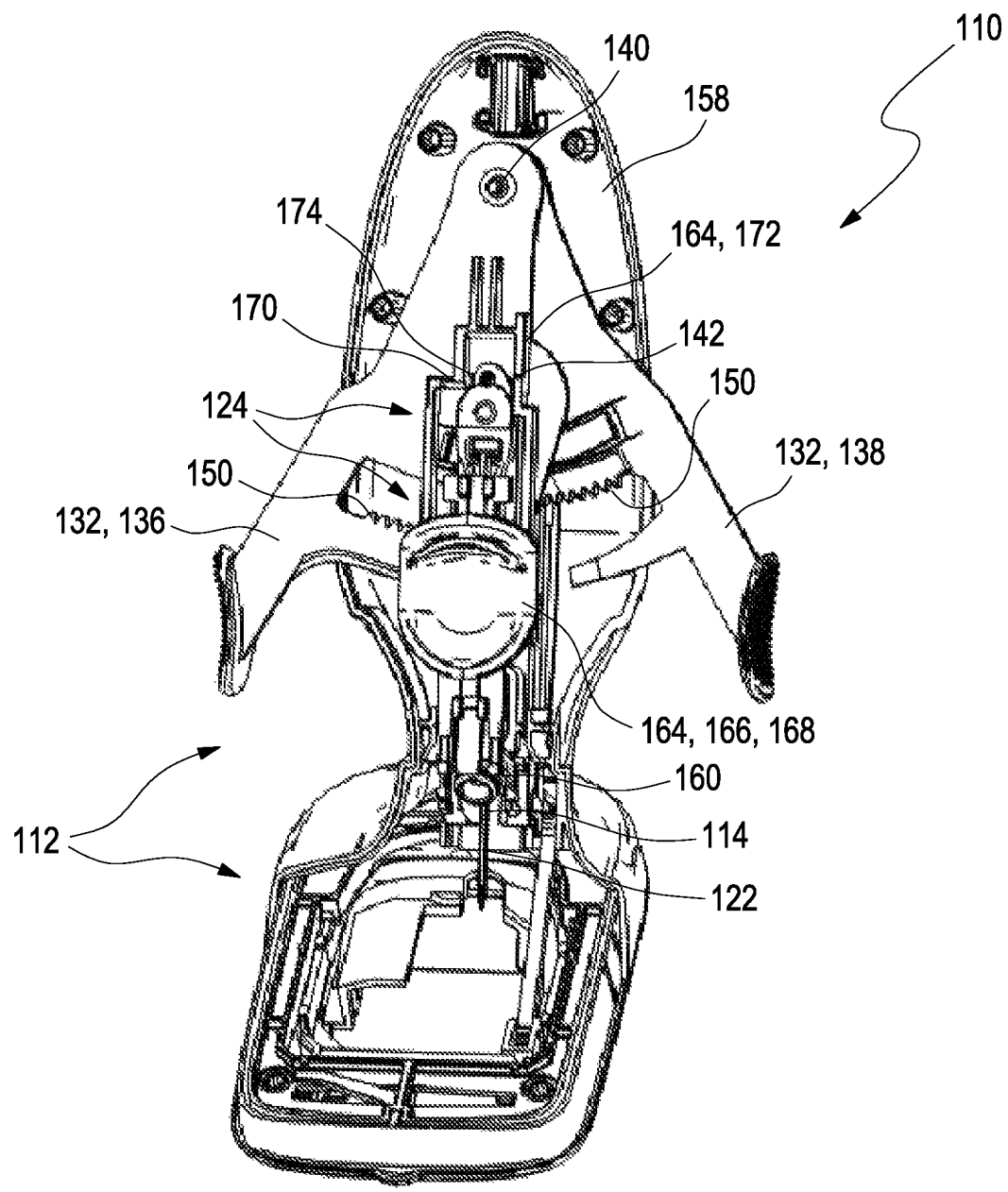
FIG. 2 shows the embodiment of FIG. 1, without the body patch.
Figure 3:
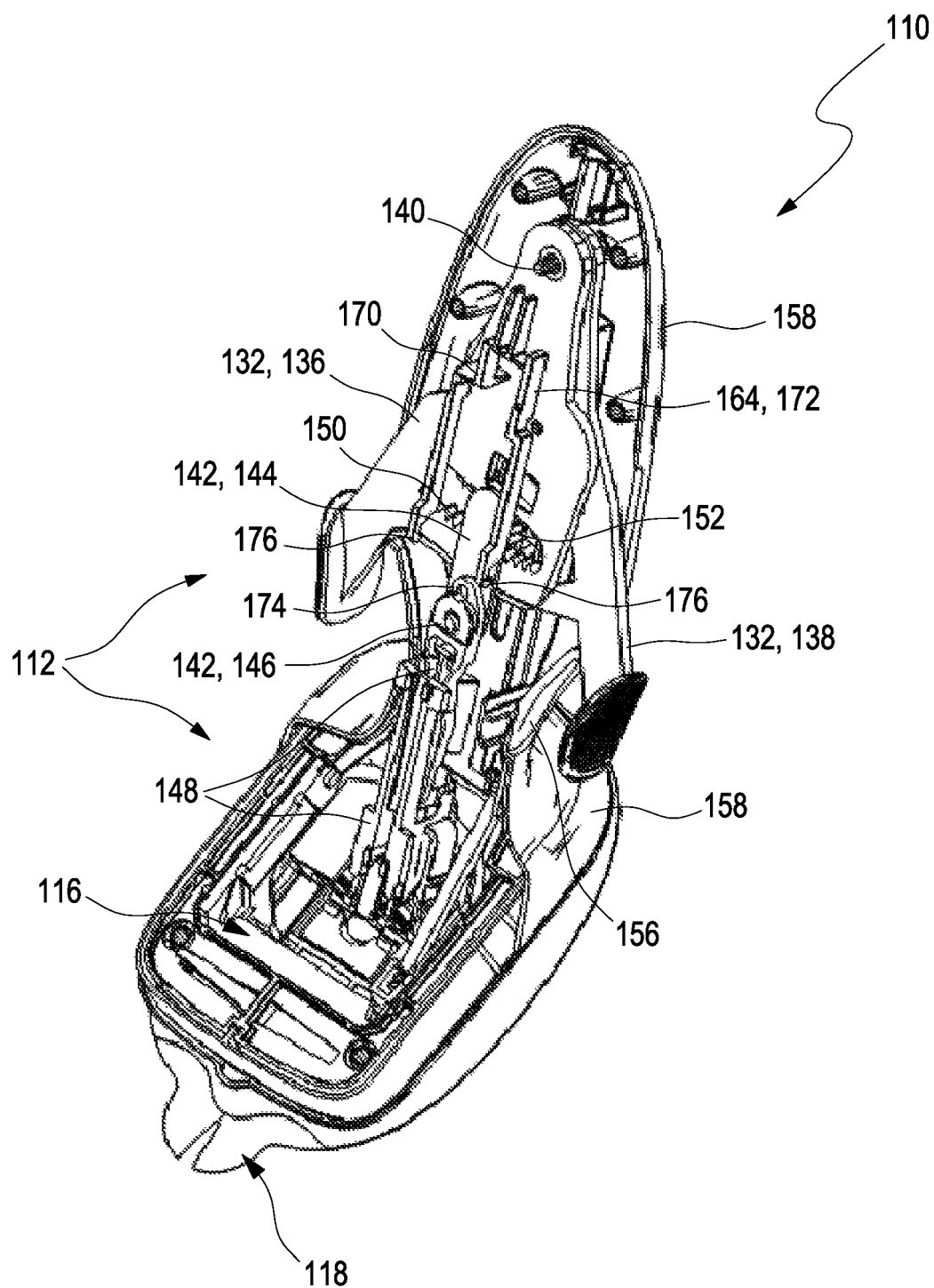
FIG. 3 shows the setup of FIG. 1 in a semi-actuated position with the insertion needle in an extended position.

As can be seen by comparing an initial position of the actuator 132 as depicted in FIG. 2 and an intermediate position of the actuator 132 with the insertion needle 122 in an extended position (the insertion needle 122 is not visible in FIG. 3), the actuator arms 136, 138 comprise toothed racks 150 adapted for interacting with a pinion 152 (visible in FIGS. 3 and 4). The pinion 152 is turned as soon as the actuator arms 136, 138 are pushed inwardly, in the actuation direction 134. Thereby, the rotor 142 is turned, driving the plunger 148 in longitudinal direction 126, whereby the insertion needle holder 120 is driven in the forward direction 128. Thus, in the position shown in FIGS. 1 and 2, which may be considered an initial position, the actuator arms 136, 138 are extended, in their initial positions. The rotor 142, consequently, is in an un-turned position, which is a twelve-o'clock-position in FIGS. 1 and 2.

Figure 5:
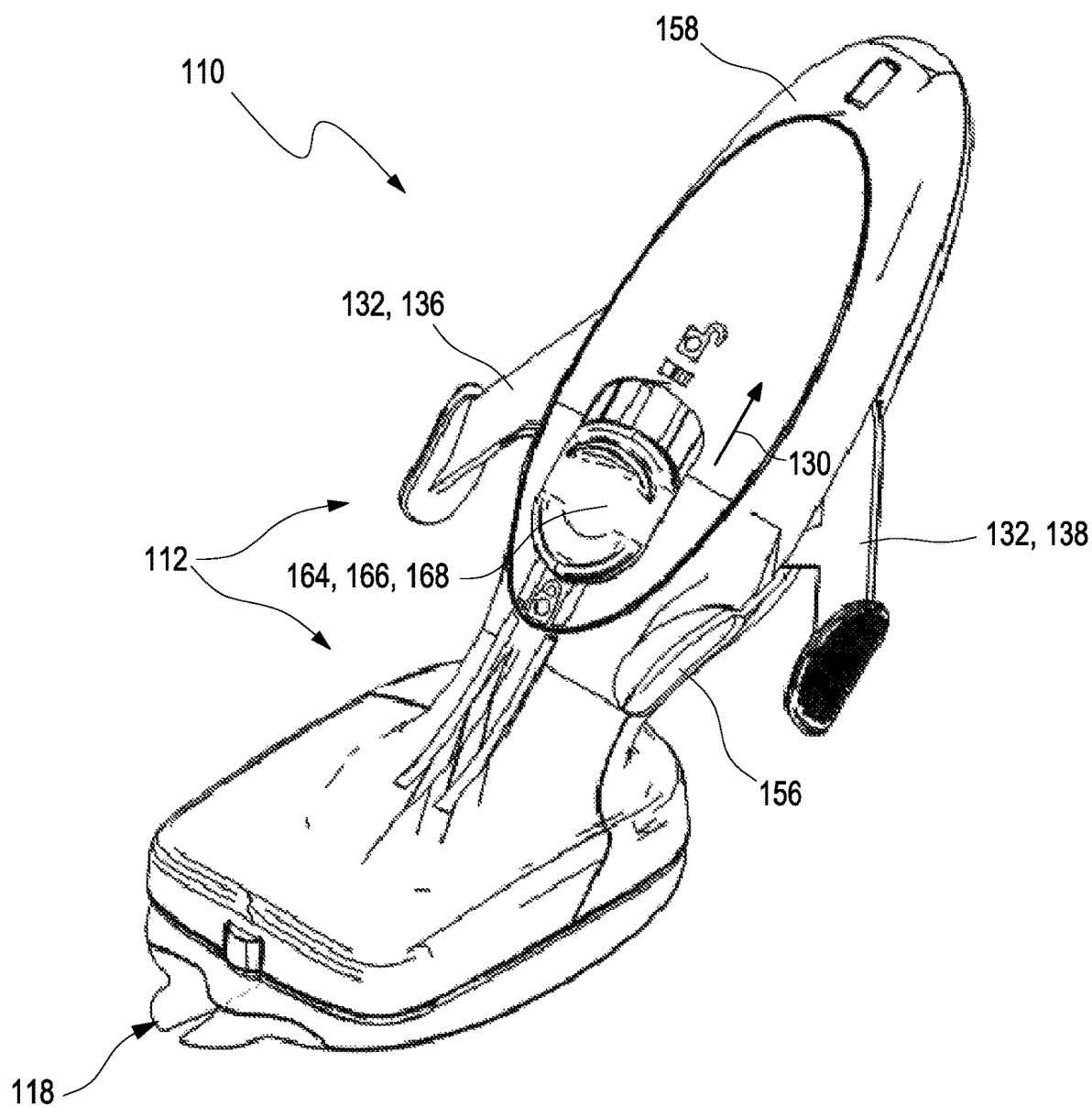
FIGS. 5A to 5C show the setup of FIG. 1 with a closed casing, in a locked position of the locking device (FIG. 5A), with the locking device in an unlocked position and the actuator partially actuated (FIG. 5B) and with the actuator in an end position (FIG. 5C)
Figure 5:
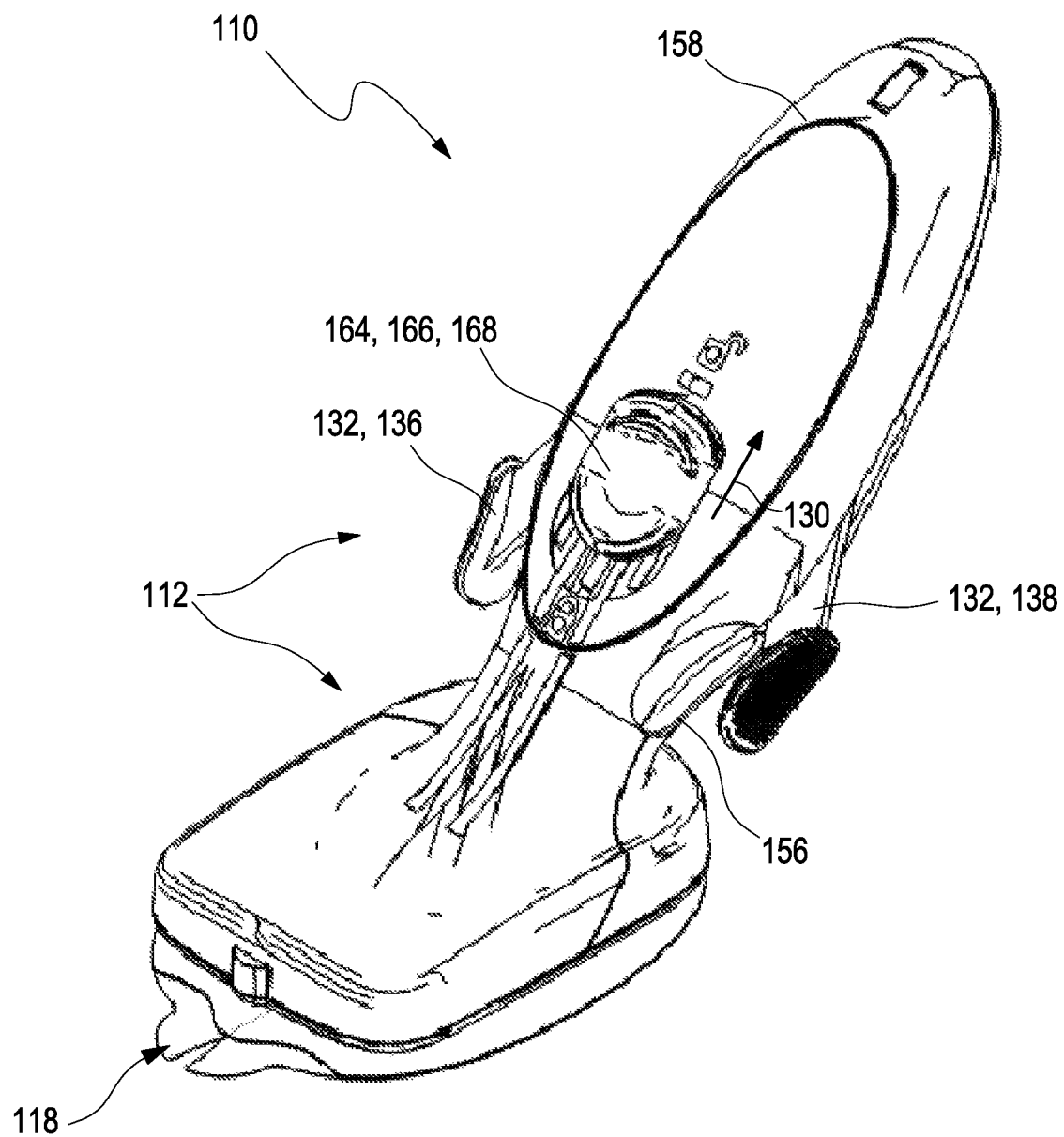
Figure 5:
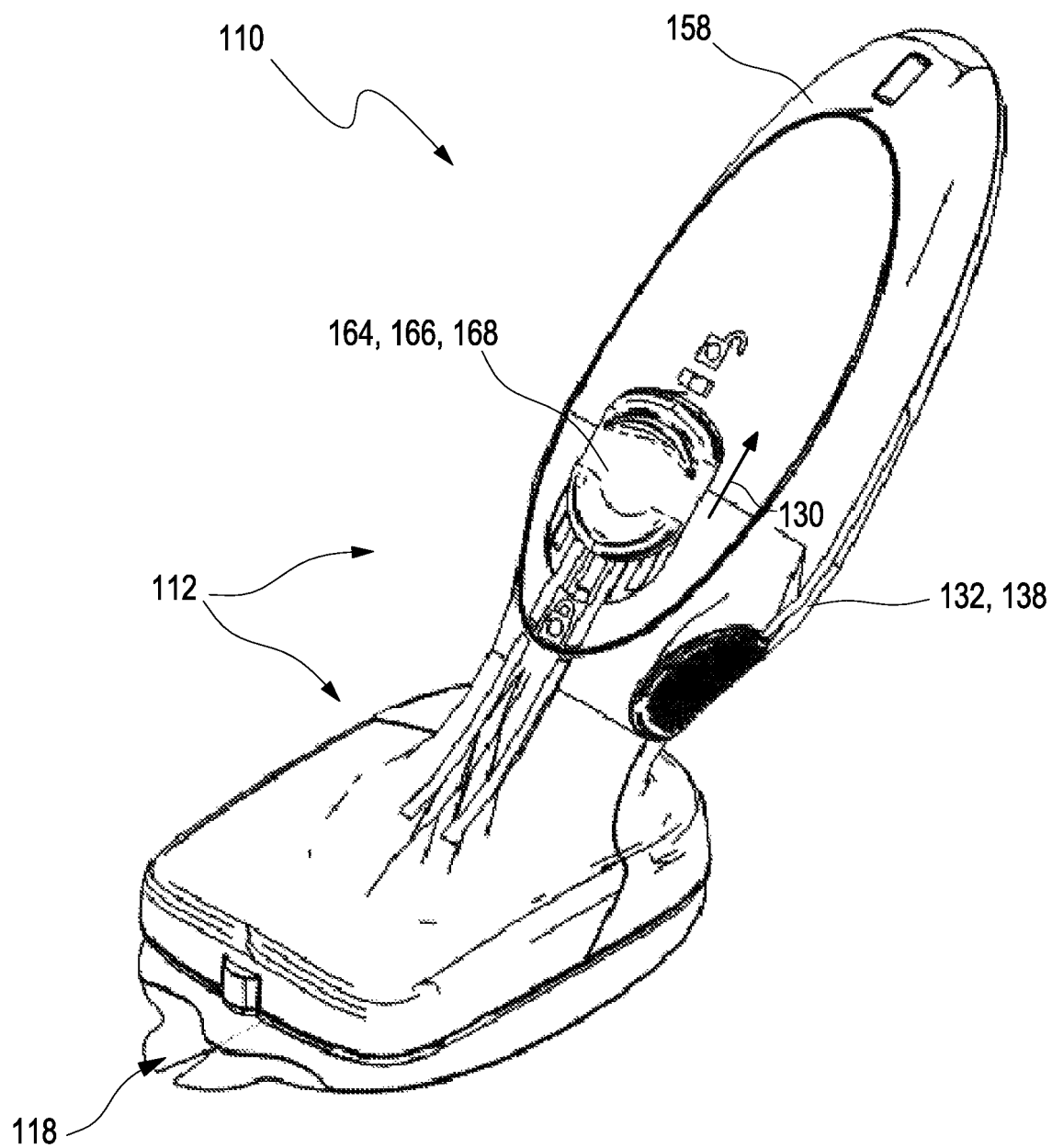

By pushing the actuator arms 136, 138 inwardly, the toothed racks 150 of these actuator arms 136, 138 interact with the pinion 152, which, again, is coupled to the rotor 142. Thereby, the rotor 142 turns in a counter-clockwise direction, thereby driving the plunger 148 in the forward direction 128, until, finally, the rotor 142 reaches the six-o'clock-position as shown in FIGS. 3 and 4. This is the position of the insertion device 110 in which the insertion needle 122 is extended into the body tissue of the user and in which the analyte sensor 114 is brought to its final position within the body tissue. By pushing the actuator arms 136, 138 further, into their actuation directions 134, the actuator arms 136, 138 finally snap into indentations 156 in a casing 158, as may be seen by comparing the initial position in FIG. 5A (corresponding to the initial positions in FIGS. 1 and 2), the intermediate position as shown in FIG. 5B (corresponding to the positions in FIGS. 3 and 4) and the final position as shown in FIG. 5C. When moving the actuator arms 136, 138 from the intermediate position as shown in FIGS. 3, 4 and 5 into the final position or rest position as shown in FIG. 5C, the rotor 142, in FIGS. 3 and 4, rotates further in a counter-clockwise direction, thereby pulling back plunger 148 and insertion needle 122, until it finally reaches its original position (twelve-o'clock-position). When retracting the insertion needle 122 from the body tissue, the analyte sensor 114 remains within the body tissue. The analyte sensor 114 is coupled to a connector 160 which specifically is visible in FIGS. 1, 2 and 4. During the downward motion of the plunger 148, i.e. during moving the actuator arms 136, 138 from the initial position in FIGS. 1 and 2 into the intermediate position in FIGS. 3 and 4, the plunger 148 pushes the connector 160 into a receptacle 162 within the body patch 116, comprising appropriate catches. Thus, when pulling back the plunger 148, the connector 160 remains within the body patch 116, and the analyte sensor 114 extends from the body patch 116 on a lower surface, into the body tissue.

The interaction of the toothed rack 150 and the pinion 152 in the exemplary embodiment shown in the Figures is one example of a gearing mechanism, which provides several advantages and which may be realized in a technically simple fashion. Other types of gearing mechanisms, however, may be used additionally or alternatively.

The insertion device 110 further comprises a safety lock 164. The safety lock 164, in a locked position, as depicted in FIGS. 1, 2 and 5A, is adapted to block a rotation of the rotor 142. The safety lock 164, in an unlocked position, as depicted in FIGS. 3, 4, 5B and 5C, is adapted to permit a rotation of the rotor and, thus, to permit a firing of the insertion device 110, implying a forward motion of the insertion needle holder 120, followed by a backward motion of the insertion needle holder 120.

For this purpose of locking, the safety lock 164 comprises an operation element 166 which, in the exemplary embodiment shown in the Figures, is designed as a slide switch 168 slidable in the longitudinal direction 126. For unlocking the safety lock 164, thereby bringing the safety lock 164 from a locked position into an unlocked position, the slide switch 168 has to be pulled back in the rearward direction 130, as shown in FIGS. 5A, 5B and 5C.

The slide switch 168 preferably may have a different color as compared to the casing 158. Thus, as an example, the casing 158 may have a white color, whereas the slide switch 168 or operation element 166 may have a blue color. Preferably, the colors of the operation element 166 and the casing 158 surrounding the operation element 166 provide a good contrast, which is easily visible for a user, such that a position of the slide switch 168 may easily be detected by eye.

The operation element 166 of the safety lock 164 is coupled to an abutment portion 170 which is visible in FIGS. 1 to 4. Thus, as an example, the safety lock 164 may comprise a shaft 172 or frame, which fully or partially is slidable within the casing 158, such that the shaft 172 with the abutment portion 170 may be moved in the longitudinal direction 126.

The abutment portion 170, as shown in FIGS. 1 and 2 (locked position), interacts with a shoulder 174 or indentation of the rotor 142, thereby preventing the rotor 142 from turning in the counter-clockwise direction. Thus, in the locked position shown in FIGS. 1 and 2 with the abutment portion 170 in its lower position, the abutment portion 170 abuts the shoulder 174, and prevents a rotation of the rotor 142.

For unlocking the safety lock 164, as explained above, the slide switch 168 is moved in the rearward direction 130. The slide switch 168 is coupled to the shaft 172, e.g. via hooks 176. These hooks 176 are visible in the FIGS. 3 and 4 in which the slide switch 168 is removed for illustrative purposes. By moving the shaft 172 upwardly in the Figures, i.e. in the rearward direction 130, the abutment portion 170 is removed from the rotor 142, such as from the shoulder 174, thereby releasing the rotor 142 and enabling or permitting a rotation of the rotor 142 in the counter-clockwise direction. Thus, by blocking or releasing a rotary movement of the rotor 142, a safe and simple locking mechanism may be provided, which may be used both for transportation purposes and for safety purposes.

In the following, specifically referring to FIGS. 6 to 8, a locking mechanism 178 of the insertion device 110 will be disclosed. The locking mechanism 178 is adapted to at least partially prevent a back-pivoting of the actuator arms 136, 138 in a direction reversing their respective actuation directions 134, once the actuator arm has been pivoted by at least one threshold angle.

Figure 6:
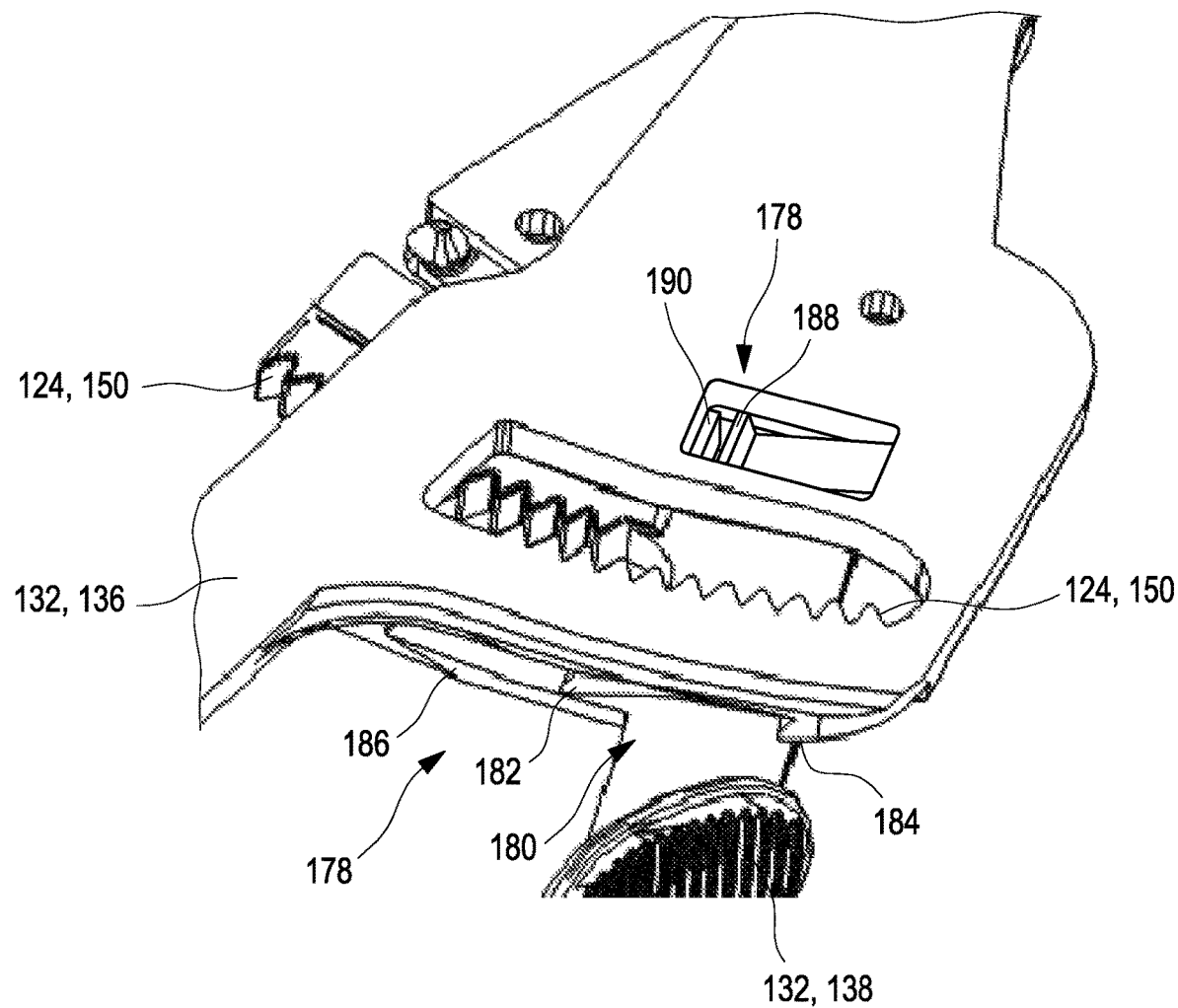
FIGS. 6 to 8 show an exemplary embodiment of a protection against reuse of the insertion device, including a locking mechanism.
Figure 7:
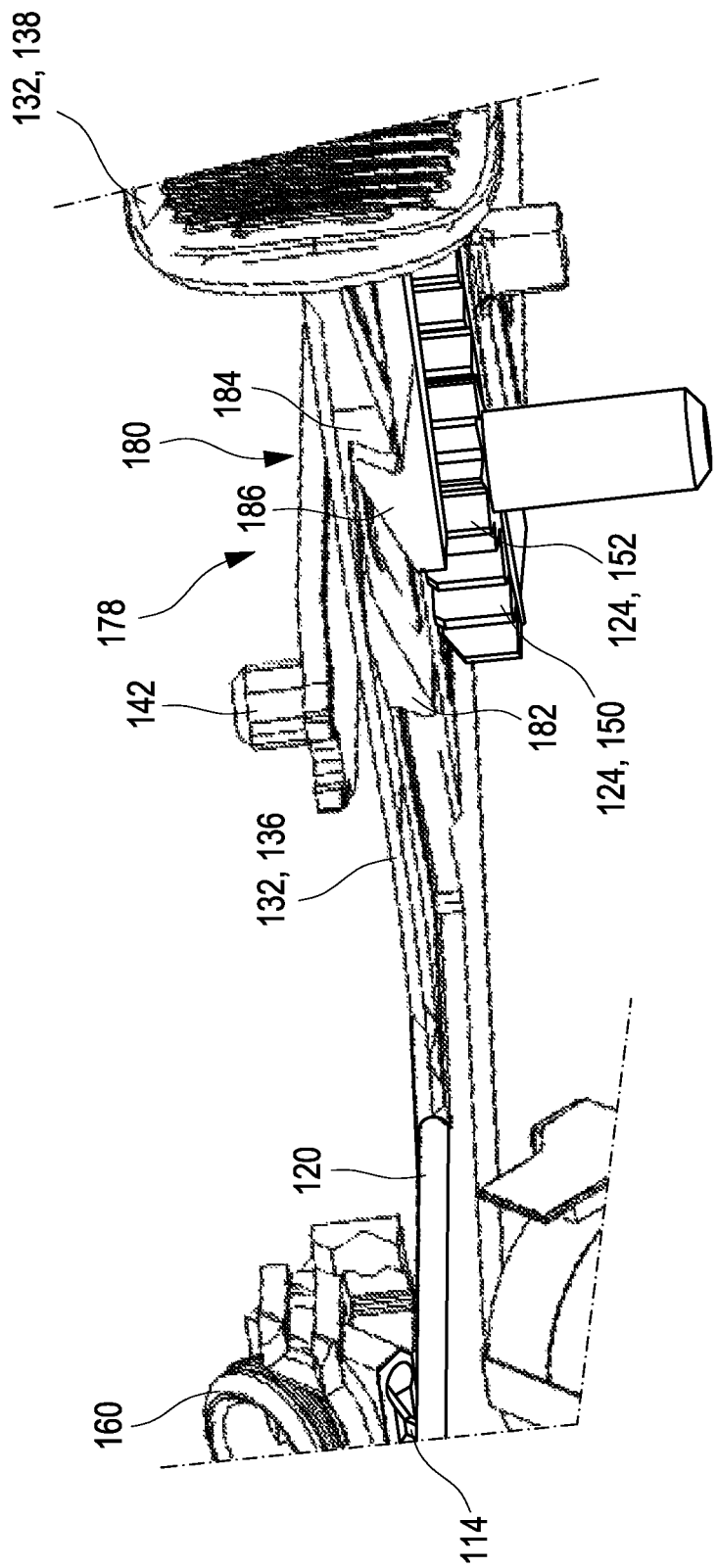
Figure 8:
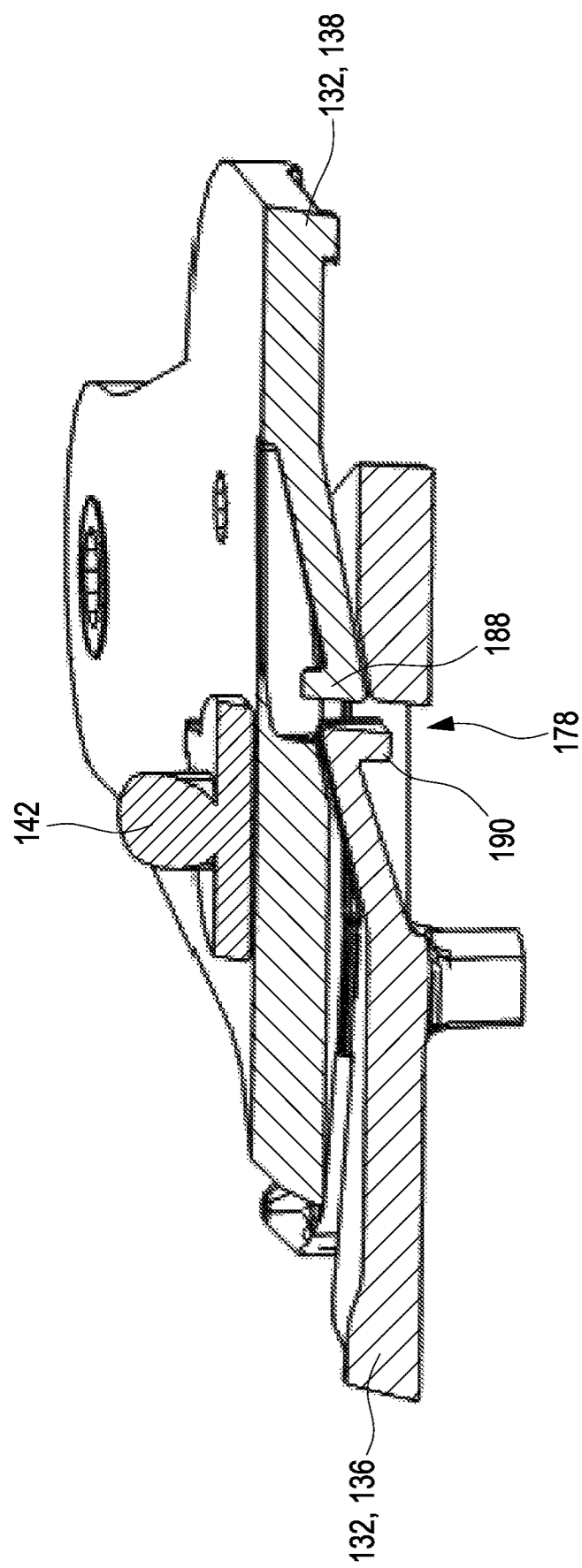
Figure 9:
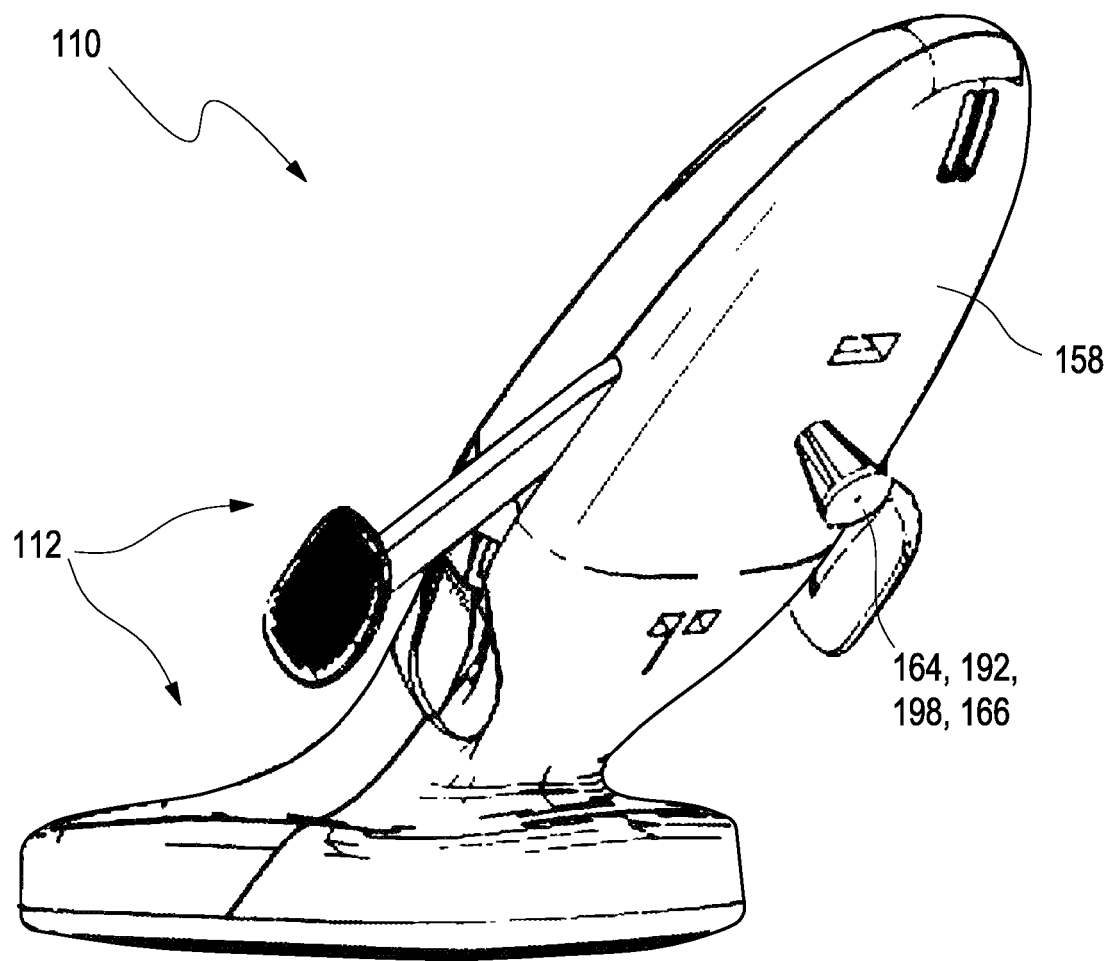
FIGS. 9A and 9B show an embodiment of the insertion device, with the safety lock comprising a pin inserted from a back side.
Figure 9:
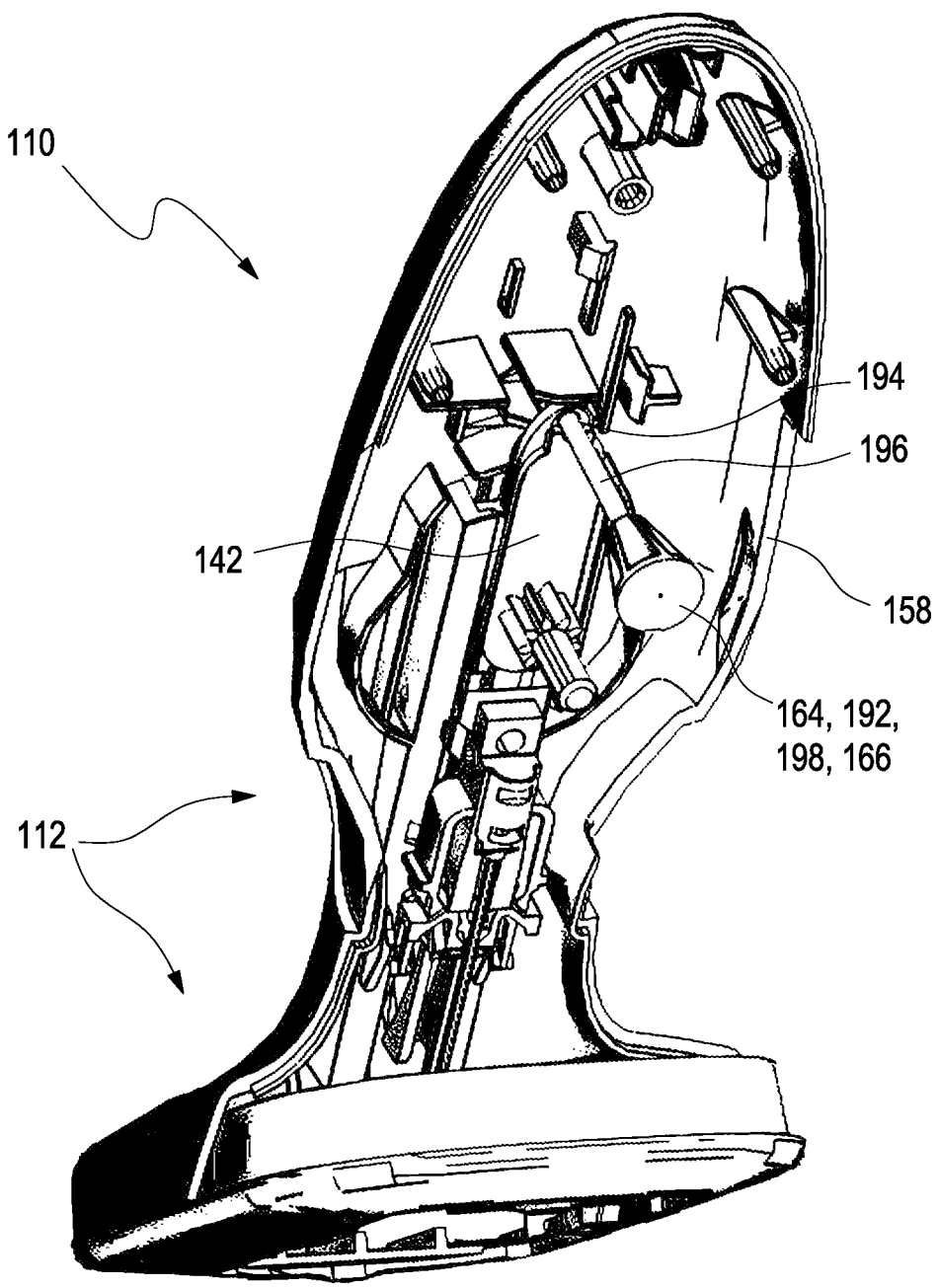
Figure 10:
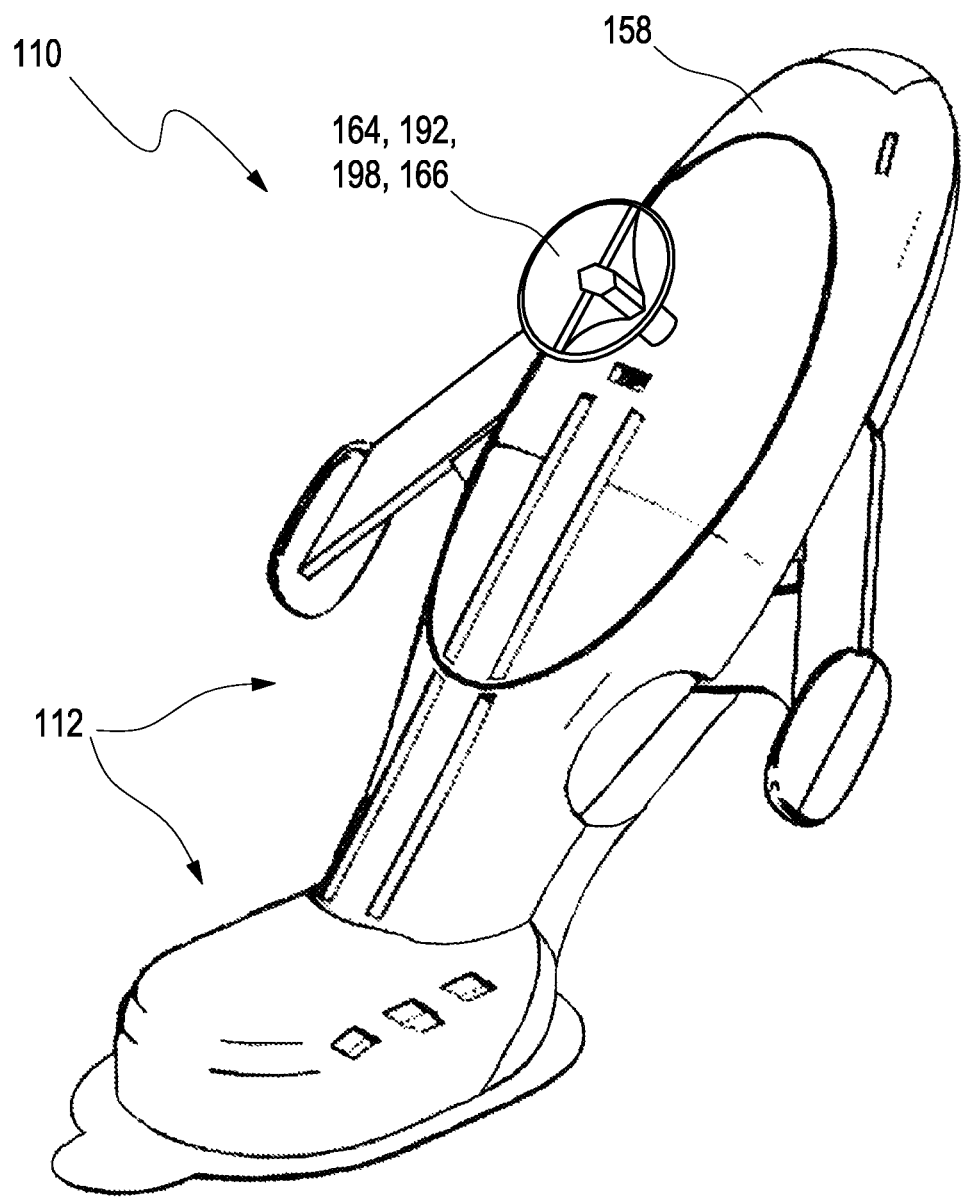
FIGS. 10A and 10B show an alternative embodiment of the insertion device, with the safety lock comprising a pin inserted from a front side.
Figure 10:
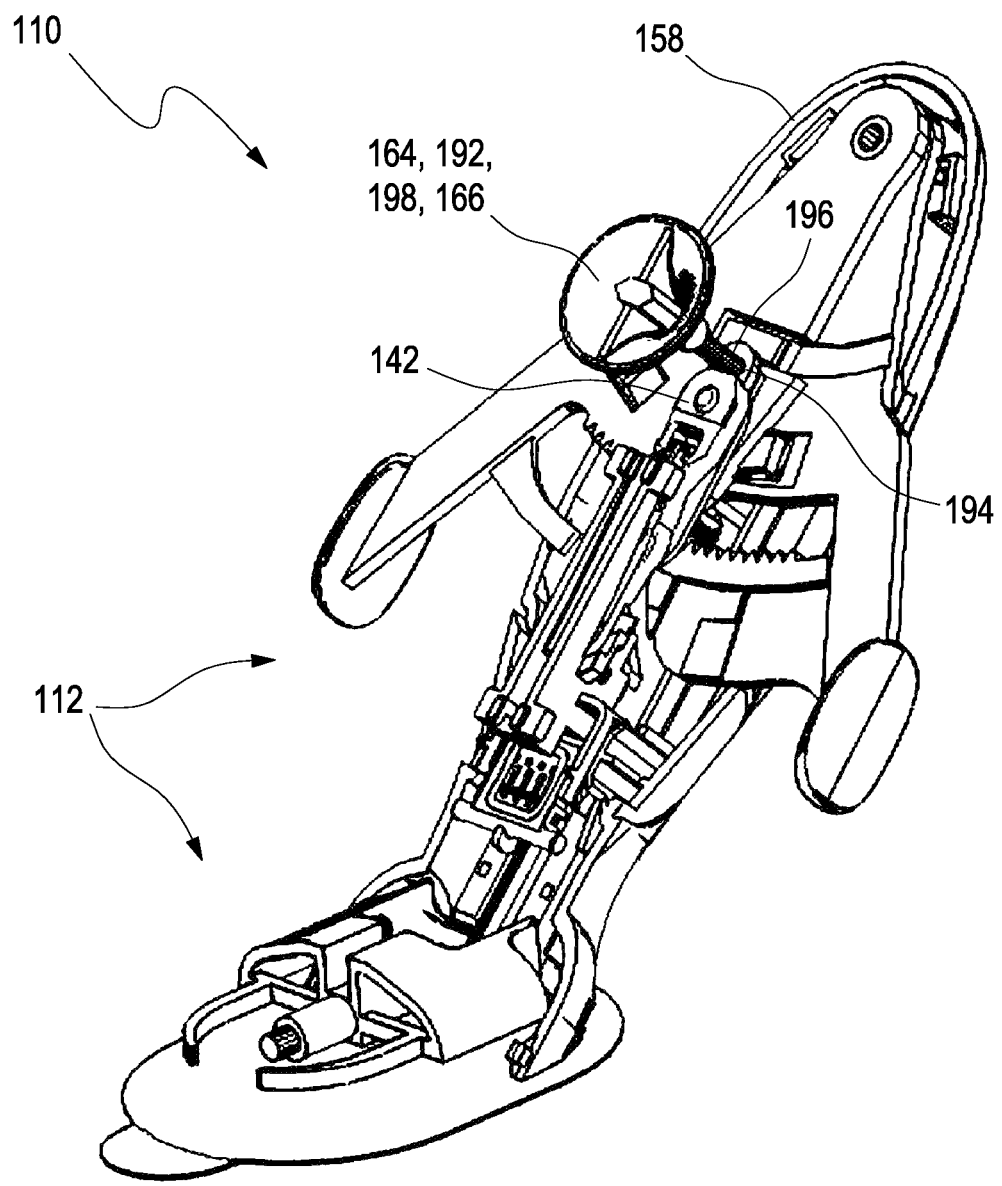

The locking mechanism 178 comprises, firstly, a ratchet mechanism 180, as visible in FIGS. 6 and 7, which, as specifically visible in FIG. 7, comprises a plurality of catches 182, 184 connected to the actuator arm 136, and a hook 186 connected to the actuator arm 138. Secondly, apart from the ratchet mechanism 180, the locking mechanism 178 may comprise catches 188, 190, as visible in FIGS. 6 and 8.

These various elements of the locking mechanism 178 fulfil several purposes. Thus, catches 182, 184, 188 and 190 define a plurality of threshold angles and locking positions, which may also be referred to as positions or angles "of no return".

Thus, catch 184 in conjunction with hook 186 defines a first, initial locking position which is visible in FIG. 7. Therein, the arms 136, 138 have been actuated far enough for hook 186 to engage with catch 184. The angular positions of actuator arms 136, 138 in this position as depicted in FIG. 7 thus define a first threshold angle or first position of no return. As outlined above, this initial position may be a position in which the actuation has been started.

Catch 182, in conjunction with hook 186, may define a second threshold angle and a second locking position. Thus, once the hook 186 has engaged with catch 182, the intermediate threshold angle and the intermediate locking position has been reached. This locking position, as an example, may correspond to an actuation state in which the insertion needle holder 120 is in its outermost position, with a maximum extension of the insertion needle 122 into the body tissue. Thereafter, in case the actuator 132 is actuated further, a backward movement of the insertion needle holder 120 takes place, with the analyte sensor 114 remaining in the body tissue. This intermediate position may prevent a reuse of the actuator 132 such that the insertion needle holder 120 with the insertion needle 122 retracts and, thereafter, may, again, perform a forward movement, thereby pushing the connector 160 of the analyte sensor 114 into the body tissue and/or destroying the connector 160 and/or the body patch 116. Thus, catch 182 in conjunction with hook 186 may prevent that the actuator arms 136, 138, once this intermediate locking position has been reached, are reopened and pushed together again, thereby retracting the insertion needle 122 and forwarding the insertion needle 122.

Finally, the locking mechanism 178 comprises above mentioned catches 188, 190. These catches 188, 190 define a final threshold angle or final locking position, also referred to as a final position of no return. As visible in FIG. 6, this final position of no return has been reached once flexible catches 188, 190 engage with each other, thereby rendering a back-pivoting of the actuator arms 136, 138 impossible. This final locking position corresponds to the final state of the actuator as depicted in FIG. 5C. In this position, the body patch 116 has been decoupled from the insertion device 110 (which means that the body patch 116 is loosely inserted into the insertion device 110 in FIG. 5C, and the insertion device 110 may be removed from the body patch 116). The final locking position with catches 188, 190 serves the purpose of keeping the contaminated insertion needle 120 within the casing 158 of the insertion device 110, thereby preventing injuries and contamination. Further, this final locking position prevents, in conjunction with the remaining parts of the locking mechanism 178, a reuse of the insertion device 110, since the actuator 132 may not be opened and re-actuated anymore.

As discussed above in the context of FIGS. 1 to 5C, the safety lock 164 specifically may comprise one or more slide switches 168 which preferably may be operated by a user. Additionally or alternatively, other types of safety locks 164 may be implemented, as will be shown in the context of FIGS. 9A to 10B. These figures show embodiments in which the safety lock 164 comprises one or more pins 192 which extend through the casing 158 of the insertion device 110, into an interior of the insertion device 110. The rotor 142 may comprise one or more openings 194 which interact with the pin 192. In the locked position, the pin is inserted into the one or more openings 194, blocking a rotation of the rotor 142. In an unlocked position, at least one pin 192 may be pulled out of the casing 158 and out of the opening 194, in order to free a rotation of the rotor 142.

Thus, in FIGS. 9A and 9B, the embodiment of the insertion device as shown in FIGS. 1 to 5C is depicted in a perspective view (FIG. 9A) and with a back side of the casing 158 removed (FIG. 9B), wherein, in addition to the slide switch 168 or as an alternative to the slide switch 168, a pin 192 is provided. As can be seen, in this embodiment, the pin 192 extends into the interior of the casing 158 from a back side and, as shown in FIG. 9B, interlocks into an opening 194 of the rotor 142. The pin 192 may manually be pulled out of the casing 158. The pin 192 may extend through the actuator arms 136 and 138, which are not shown in FIG. 9A for the sake of simplicity.

The pin 192 may comprise an elongated portion 196, such as a cylindrical portion, and, additionally, may comprise a handling portion 184. The handling portion 184 may be located outside the housing 158 and may be adapted for being grabbed by the fingers of the user, in order to pull out the pin 192 from the casing, in order to bring the insertion device 110 into the unlocked position. Thus, the handling portion 184 may function as an operation element 166. The elongated portion 196, on the other hand, which interacts with the opening 194 in order to block the rotor 142 in the locked position, may function as a locking or blocking element of the safety lock 164.

For the remaining parts of the embodiment shown in FIGS. 9A and 9B, reference may be made to the description of FIGS. 1 to 5C above.

In an alternative embodiment shown in FIG. 10A (perspective front view with casing 158 closed) and 10B (perspective front view with casing 158 partially opened), the pin 192 may be inserted from a front side of the insertion device 110. Again, the pin 192 may comprise a handling portion 184 and an elongated portion 196, wherein the latter may interact with an opening 194 of the rotor 142.

Again, for the remaining parts of the embodiment shown in FIGS. 10A and 10B, reference may be made to the description of FIGS. 1 to 5C above. It shall be noted, however, that various combinations of the safety lock 164 are feasible, such as embodiments comprising the slide switch 168, only, embodiments comprising the pin 192, only, and embodiments comprising both the slide switch 168 and the pin 192.

LIST OF REFERENCE NUMBERS 110 insertion device
112 insertion kit
114 analyte sensor
116 body patch
118 adhesive plaster
120 insertion needle holder
122 insertion needle
124 drive mechanism
126 longitudinal direction
128 forward direction
130 rearward direction
132 actuator
134 actuation direction
136 actuator arm
138 actuator arm
140 axle
142 rotor
144 first rotor part
146 second rotor part
148 plunger
150 toothed rack
152 pinion 156 indentations
158 casing
160 connector
162 receptacle
164 safety lock
166 operation element
168 slide switch
170 abutment portion
172 shaft
174 shoulder
176 hook
178 locking mechanism
180 ratchet mechanism
182 catch
184 catch
186 hook
188 catch
190 catch
192 pin
194 opening
196 elongated portion
198 handling portion

The invention claimed is:

1. An insertion device for inserting an analyte sensor into a body tissue, the insertion device comprising:
   an insertion needle holder;
   a drive mechanism for linearly driving the insertion needle holder in a longitudinal direction; and
   at least one actuator for actuating the drive mechanism, the actuator comprising a first actuator arm pivotable in a first actuation direction and a second actuator arm pivotable in a second actuation direction to actuate the drive mechanism, the first actuation direction opposing the second actuation direction, the first actuator arm comprising at least one first locking part and the second actuator arm comprising at least one second locking part,
   the first locking part and the second locking part engaging once the first and second actuator arms have been pivoted by at least one threshold angle, the engagement protecting against reuse at least partially preventing a back-pivoting of the actuator arms in directions reversing the actuation directions once the actuator arms have been pivoted by the at least one threshold angle,
   wherein the actuator arms are configured to be locked in at least two locking positions.

2. The insertion device according to claim 1, wherein the locking positions comprise an initial locking position in which the actuator arms are configured to be locked after initial activation and an end locking position in which the actuator arms are configured to be locked after full actuation of the actuator.

3. The insertion device according to claim 2, wherein the locking positions comprise at least one intermediate locking position in between the initial locking position and, the end locking position.

4. The insertion device according to claim 1, wherein the locking mechanism comprises at least one element selected from the group consisting of: a catch, a hook, a latch, a hook, a pawl, a ratchet.

5. The insertion device according to claim 1, wherein one or both of the first locking part and the second locking part form at least one ratchet mechanism.

6. The insertion device according to claim 1, wherein the first locking part and the second locking part comprise flexible locking parts.

7. The insertion device according to claim 1, wherein the first locking part and the second locking part comprise elements at least partially made of a plastic material.

8. An insertion kit for inserting an analyte sensor into a body tissue, comprising:
   at least one insertion device, the insertion device including
   an insertion needle holder;
   a drive mechanism for linearly driving the insertion needle holder in a longitudinal direction; and
   at least one actuator for actuating the drive mechanism, the actuator comprising a first actuator arm pivotable in a first actuation direction and a second actuator arm pivotable in a second actuation direction to actuate the drive mechanism, the first actuation direction opposing the second actuation direction, the first actuator arm comprising at least one first locking part and the second actuator arm comprising at least one second locking part,
   the first locking part and the second locking part engaging once the first and second actuator arms have been pivoted by at least one threshold angle, the engagement protecting against reuse at least partially preventing a back-pivoting of the actuator arms in directions reversing the actuation directions once the actuator arms have been pivoted by the at least one threshold angle,
   wherein the actuator arms are configured to be locked in at least two locking positions; and
   at least one analyte sensor.

9. The insertion kit according to claim 8, further comprising at least one body patch adapted for attachment to a skin surface, wherein the body patch is adapted to be coupled to the insertion device during inserting the analyte sensor into the body tissue.

10. The insertion kit according to claim 9, wherein the body patch is further adapted to be decoupled from the insertion device after insertion.

11. The insertion kit according to claim 9, wherein the analyte sensor comprises at least one mounting part, wherein the insertion kit is adapted to couple the mounting part to the body patch during insertion.

12. A method for inserting an analyte sensor into a body tissue, the method comprising using an insertion device comprising:
   an insertion holder;
   a drive mechanism for linearly driving the insertion needle holder in a longitudinal direction; and
   at least one actuator for actuating the drive mechanism, the actuator comprising a first actuator arm pivotable in a first actuation direction and a second actuator arm pivotable in a second actuation direction to actuate the drive mechanism, the first actuation direction opposing the second actuation direction, the first actuator arm comprising at least one first locking part and the second actuator arm comprising at least one second locking part,
   the first locking part and the second locking part engaging once the first and second actuator arms have been pivoted by at least one threshold angle, the engagement protecting against reuse at least partially preventing a back-pivoting of the actuator arms in directions reversing the actuation directions once the actuator arms have been pivoted by the at least one threshold angle, wherein the actuator arms are configured to be locked in at least two locking positions.

\* \* \* \* \*